(12) United States Patent
Marotta et al.

(10) Patent No.: US 6,261,305 B1
(45) Date of Patent: Jul. 17, 2001

(54) ENDOVASCULAR PROTHESIS WITH EXPANDABLE LEAF PORTION

(75) Inventors: Thomas R. Marotta, North Vancouver (CA); George A. Shukov, Los Altos Hills, CA (US); Donald R. Ricci; Ian M. Penn, both of Vancouver (CA)

(73) Assignee: eClips Systems Inc. (CA)

( * ) Notice: Subject to any disclaimer, the term of this patent is extended or adjusted under 35 U.S.C. 154(b) by 0 days.

(21) Appl. No.: 09/249,102

(22) Filed: Feb. 12, 1999

Related U.S. Application Data

(60) Provisional application No. 60/074,521, filed on Feb. 12, 1998.

(51) Int. Cl.[7] .............................. A61M 29/00; A61F 2/06
(52) U.S. Cl. ...................... 606/200; 623/1.15; 623/1.37
(58) Field of Search ................................. 623/1.15, 1.17, 623/1.3, 1.37, 1.2, 1.24, 1.25, 1.26; 606/200

(56) References Cited

U.S. PATENT DOCUMENTS

| | | | |
|---|---|---|---|
| 5,411,552 | * | 5/1995 | Andersen et al. .................. 623/1.26 |
| 5,500,014 | * | 3/1996 | Quijano et al. ..................... 623/1.26 |
| 5,609,628 | | 3/1997 | Keranen .................................... 623/1 |
| 5,891,195 | * | 4/1999 | Klostermeyer et al. ............ 623/1.26 |
| 6,093,199 | * | 7/2000 | Brown et al. ........................ 606/200 |
| 6,096,071 | * | 8/2000 | Yadav ................................. 623/1.15 |
| 6,099,549 | * | 8/2000 | Bosma et al. ....................... 606/200 |

* cited by examiner

Primary Examiner—David H. Willse
Assistant Examiner—Suzette J. Jackson
(74) Attorney, Agent, or Firm—Katten Muchin Zavis

(57) ABSTRACT

A novel endovascular approach useful in the treatment of aneurysms, particularly saccular aneurysms. The present endovascular prosthesis comprises a leaf portion capable of being urged against and blocking the opening of the aneurysm thereby leading to obliteration of the aneurysm. The leaf portion is attached to, and independently moveable with respect to, a body comprising at least one expandable portion. Thus, the body serves the general purpose of fixing the endovascular prosthesis in place at a target body passageway in the vicinity at which the aneurysm is located and the leaf portion serves the purpose of blocking the aneurysmal opening thereby leading to obliteration of the aneurysm. A method of delivering and implanting the endovascular prosthesis is also described.

27 Claims, 19 Drawing Sheets

ENDOVASCULAR PROTHESIS WITH EXPANDABLE LEAF PORTION

This application claims benefit under 35 U.S.C § 119(e) of U.S. Provisional Application No. 60/074,521, filed Feb. 12, 1998.

BACKGROUND OF THE INVENTION

1. Field of the Invention

In one of its aspects, the present invention relates to an endovascular prosthesis. In another of its aspects, the present invention relates to a method of treating an aneurysm in a patient.

2. Description of the Prior Art

As is known in the art, an aneurysm is an abnormal bulging outward in the wall of an artery. In some cases, the bulging may be in the form of a smooth bulge outward in all directions from the artery—this is known as a "fusiform aneurysm". In other cases, the bulging may be in the form of a sac arising from an arterial branching point or from one side of the artery—this is known as a "saccular aneurysm".

While aneurysms can occur in any artery of the body, those which occur in the brain can lead to the occurrence of a stroke. Most saccular aneurysms which occur in the brain have a neck which extends from the cerebral blood vessel and broadens into a pouch which projects away from the vessel.

The problems caused by such aneurysms can occur in several different ways. For example, if the aneurysm ruptures, blood enters the brain or the subarachnoid space (i.e., the space closely surrounding the brain)—the latter is known as aneurysmal subarachnoid hemorrhage. This followed by one or more of the following symptoms: nausea, vomiting, double vision, neck stiffness and loss of consciousness. Aneurysmal subarachnoid hemorrhage is an emergency medical condition requiring immediate treatment. Indeed, 10–15% of patients with the condition die before reaching the hospital for treatment. More than 50% of patients with the condition will die within the first thirty days after the hemorrhage. Of those patients who survive, approximately half will suffer a permanent stroke. It is typical for such a stroke to occur one to two weeks after the hemorrhage itself from vasospasm in cerebral vessels induced by the subarachnoid hemorrhage. Aneurysms also can cause problems which are not related to bleeding although this is less common. For example, an aneurysm can form a blood clot within itself which can break away from the aneurysm and be carried downstream where it has the potential to obstruct an arterial branch causing a stroke. Further, the aneurysm can also press against nerves (this has the potential of resulting in paralysis or abnormal sensation of one eye or of the face) or the adjacent brain (this has the potential of resulting in seizures).

Given the potentially fatal consequences of the aneurysms, particularly brain aneurysms, the art has addressed treatment of aneurysms using various approaches.

Generally, aneurysms may be treated from outside the blood vessels using surgical techniques or from the inside using endovascular techniques (the latter falls under the broad heading of interventional (i.e., non-surgical) techniques).

Surgical techniques usually involve a craniotomy requiring creation of an opening in the skull of the patient through which the surgeon can insert instruments to operate directly on the brain. In one approach, the brain is retracted to expose the vessels from which the aneurysm arises and then the surgeon places a clip across the neck of the aneurysm thereby preventing arterial blood from entering the aneurysm. If there is a clot in the aneurysm, the clip also prevents the clot from entering the artery and obviates the occurrence of a stroke. Upon correct placement of the clip the aneurysm will be obliterated in a matter of minutes. Surgical techniques are the most common treatment for aneurysms. Unfortunately, surgical techniques for treating these conditions are regarded as major surgery involving high risk to the patient and necessitate that the patient have strength even to have a chance to survive the procedure.

As discussed above, endovascular techniques are non-surgical techniques and are typically performed in an angiography suite using a catheter delivery system. Specifically, known endovascular techniques involve using the catheter delivery system to pack the aneurysm with a material which prevents arterial blood from entering the aneurysm—this technique is broadly known as embolization. One example of such an approach is the Guglielmi Detachable Coil which involves intra-aneurysmal occlusion of the aneurysm via a system which utilizes a platinum coil attached to a stainless steel delivery wire and electrolytic detachment. Thus, once the platinum coil has been placed in the aneurysm, it is detached from the stainless steel delivery wire by electrolytic dissolution. Specifically, the patient's blood and the saline infusate act as the conductive solutions. The anode is the stainless steel delivery wire and the cathode is the ground needle which is placed in the patient's groin. Once current is transmitted through the stainless steel delivery wire, electrolytic dissolution will occur in the uninsulated section of the stainless steel detachment zone just proximal to the platinum coil (the platinum coil is of course unaffected by electrolysis). Other approaches involve the use of materials such as cellulose acetate polymer to fill the aneurysm sac. While these endovascular approaches are an advance in the art, they are disadvantageous. Specifically, the risks of these endovascular approaches include rupturing the aneurysm during the procedure or causing a stroke due to distal embolization of the device or clot from the aneurysm. Additionally, concern exists regarding the long term results of endovascular aneurysm obliteration using these techniques. Specifically, there is evidence of intra-aneurysmal rearrangement of the packing material and reappearance of the aneurysm on follow-up angiography.

One particular type of brain aneurysm which has proven to be very difficult to treat, particularly using the surgical clipping or endovascular embolization techniques discussed above occurs at the distal basilar artery. This type of aneurysm is a weak outpouching, usually located at the terminal bifurcation of the basilar artery. Successful treatment of this type of aneurysm is very difficult due, at least in part, to the imperative requirement that all the brainstem perforating vessels be spared during surgical clip placement.

Unfortunately, there are occasions when the size, shape and/or location of an aneurysm make both surgical clipping and endovascular embolization not possible for a particular patient. Generally, the prognosis for such patients is not good.

Accordingly, while the prior art has made advances in the area of treatment of aneurysms, there is still room for improvement, particularly in endovascular embolization since it is such an attractive alternative to major surgery. Specifically, it would be desirable to have an endovascular prosthesis which could be used in the embolization of aneurysms which are difficult or not possible to treat otherwise. It would be further desirable if such an endovascular prosthesis could be used to treat aneurysms currently treated endovascularly while mitigating or obviating the disadvantages associated with current endovascular embolization techniques.

SUMMARY OF THE INVENTION

It is an object of the present invention to provide a novel endovascular prosthesis which obviates or mitigates at least one of the above-mentioned disadvantages of the prior art.

It is another object of the present invention to provide a novel method for endovascular blocking an aneurysmal opening which obviates or mitigates at least one of the above-mentioned disadvantages of the prior art.

Accordingly, in one of its aspects, the present invention relates to a prosthesis for endovascular blocking of an aneurysmal opening, the prosthesis comprising:

a body having a promixal end, a distal end and at least one expandable portion disposed therebetween, the at least one expandable portion being expandable from a first, unexpanded state to a second, expanded state with a radially outward force thereon to urge the first expandable portion against a vascular lumen, and a leaf portion attached to the body, the leaf portion being independently moveable with respect to the body.

In another of its aspects, the present invention relates to a prosthesis for endovascular blocking of an aneurysmal, the prosthesis comprising:

a body having a promixal end, a distal end and at least one expandable portion disposed therebetween, the at least one expandable portion being expandable from a first, unexpanded state to a second, expanded state with a radially outward force thereon to urge the first expandable portion against a vascular lumen, and a leaf portion attached to the body, the body being flexible between: (i) a first position in which the proximal end, the distal end and the leaf portion are aligned along a longitudinal axis of the body, and (ii) a second position in which the leaf portion is aligned with only one of the distal end and the proximal end along the longitudinal axis.

In yet another of its aspects, the present invention relates to a prosthesis for endovascular blocking of an aneurysmal opening, the prosthesis comprising:

a body having a longitudinal axis comprising at least one expandable portion, the at least one expandable portion being expandable from a first, unexpanded state to a second, expanded state with a radially outward force thereon to urge the first expandable portion against a vascular lumen, and a leaf portion attached to the body, the body being flexible between: (i) a first position in which the at least one expandable portion and the leaf portion are aligned along the longitudinal axis, and (ii) a second position in which the at least one expandable portion and the leaf are unaligned along the longitudinal axis.

In yet another of its aspects, the present invention relates to a method for endovascular blocking of an aneurysmal opening with a prosthesis comprising: a body having a promixal end, a distal end and at least one expandable portion disposed therebetween, and a leaf portion attached to the body, the method comprising the steps of:

disposing the prosthesis on a catheter;

inserting the prosthesis and catheter within a body passageway by catheterization of the body passageway;

translating the prosthesis and catheter to a target body passageway at which the aneurysm opening is located;

exerting a radially outward expansive force on the at least one expandable portion such that the at least one expandable portion is urged against the target body passageway.

urging the leaf portion against the aneurysmal opening thereby blocking the aneurysmal opening.

Thus, the present inventors have discovered a novel endovascular approach useful in blocking of an aneurysmal opening, particularly those in saccular aneurysms, leading to obliteration of the aneurysm. The approach is truly endovascular in that, with the present endovascular prosthesis, there is no requirement to pack the aneurysmal sac with a material (e.g., such is used with the Guglielmi Detachable Coil). Rather, the present endovascular prosthesis operates on the basis that it serves to block the opening to the aneurysmal sac thereby obviating the need for packing material. Thus, a novel endovascular prosthesis has been discovered which obviates or mitigates many of the disadvantages of the prior art. The present endovascular prosthesis comprises a leaf portion capable of being urged against the opening of the aneurysm thereby closing the aneurysm. The leaf portion is attached to, and independently moveable with respect to, a body comprising at least one expandable portion. The tubular portion is expandable from a first, unexpanded state to a second, expanded stated with a radially outward force thereon to urge the first expandable portion against a vascular lumen. Thus, the body serves the general purpose of fixing the endovascular prosthesis in place at a target vascular lumen body passageway in the vicinity at which the aneurysmal opening is located and the leaf portion serves the purpose of sealing the aneurysmal opening thereby leading to obliteration of the aneurysm. Thus, as will be developed further hereinbelow, the leaf portion functions and is moveable independently of the body of the endovascular prosthesis.

Preferably, and as will be further developed hereinbelow, the at least one expandable portion is generally tubular in structure. Indeed, throughout this specification, reference will be made to an expandable portion which is generally tubular in structure. However, such reference is for illustrative purposes only and those of skill in the art will recognize that it is possible to utilize a non-tubular structure (e.g., a claw-like design which opens upon expansion) as the at least one expandable portion.

The body of the present endovascular prosthesis has a generally longitudinal axis and is flexible. The leaf portion is independently moveable between at least a first position and a second position with respect to the body, expanded or unexpanded. Thus, in the first position, the distal end and the proximal end of the body are aligned with the leaf portion. In the second position, while securing the distal end and the proximal end of the body, the leaf portion maintains a degree of independent movement. In this manner, the leaf portion is "independently moveable" with respect to the body. In one embodiment, it is preferred that this independent movement is achieved by disposing the leaf portion such that it may pivot with respect to the remainder of the endovascular prosthesis. It should be understood that, while the leaf portion is independently moveable with respect to the body, the final alignment of the distal end, the proximal end and leaf portion (i.e., the alignment after blockage of the aneurysmal opening) is not particularly restricted and depends on factors such as the size and location of the aneurysm and the anatomy of the particular patient. The key point is that the leaf portion is capable of being independently moved with respect to the body.

In one preferred embodiment, the body is in the form of a flexible tube, preferably a flexible, porous tube. In this embodiment, the leaf portion may be a cut-out along the length of the tube and at least one, preferably both, ends of the tube are expandable upon application of a radially outward force thereon to fix the tube in place in the target body passageway. The leaf portion is capable of moving out of the plane of the tube upon flexure of the tube and/or expansion of the tube in a radially outward direction to be urged against an opening of and thereby blocking the aneurysmal opening.

In another preferred embodiment, the body is in the form of a pair of opposed tubular or ring-like sections which are connected to one another. The leaf portion is connected to one or both of the tubular or ring-like sections. The ring-like sections are expandable upon exertion (e.g., applied by a catheter-mounted balloon or inherent in a self-expanding device) of a radially outward force thereon to urge fix the body in place in the target body passageway. As is known in the art, it is possible to confer expandability to the ring-like sections by designing these sections to have a porous surface (e.g., comprising a plurality of interconnecting struts). For materials such as stainless steel, this allows the ring-like structures to expand prior to reaching the point of plastic deformation. The leaf portion is capable of moving out of the plane of the tube upon flexure of the tube and/or expansion of the tube in a radially outward direction.

The present endovascular prosthesis is believed to provide a significant alternative the conventional surgical techniques described hereinabove. Additionally, it is envisaged that the present endovascular prosthesis may used in the treatment of certain aneurysms which are diagnosed as being inoperable. The present endovascular prosthesis also is believed to provide a significant advantage of current endovascular approaches such as the Guglielmi Detachable Coil described hereinabove. Specifically, since the present endovascular prosthesis does not rely on insertion into the aneurysm of a metal packing material (e.g., platinum coil), the risk of rupturing the aneurysm is mitigated as is the risk of intra-aneurysmal rearrangement of the metal packing material and subsequent reappearance of the aneurysm.

BRIEF DESCRIPTION OF THE DRAWINGS

Embodiments of the present invention will be described with reference to the accompanying drawings, wherein like reference numerals denote like elements and in which.

DETAILED DESCRIPTION OF THE PREFERRED EMBODIMENTS

Figure 1:
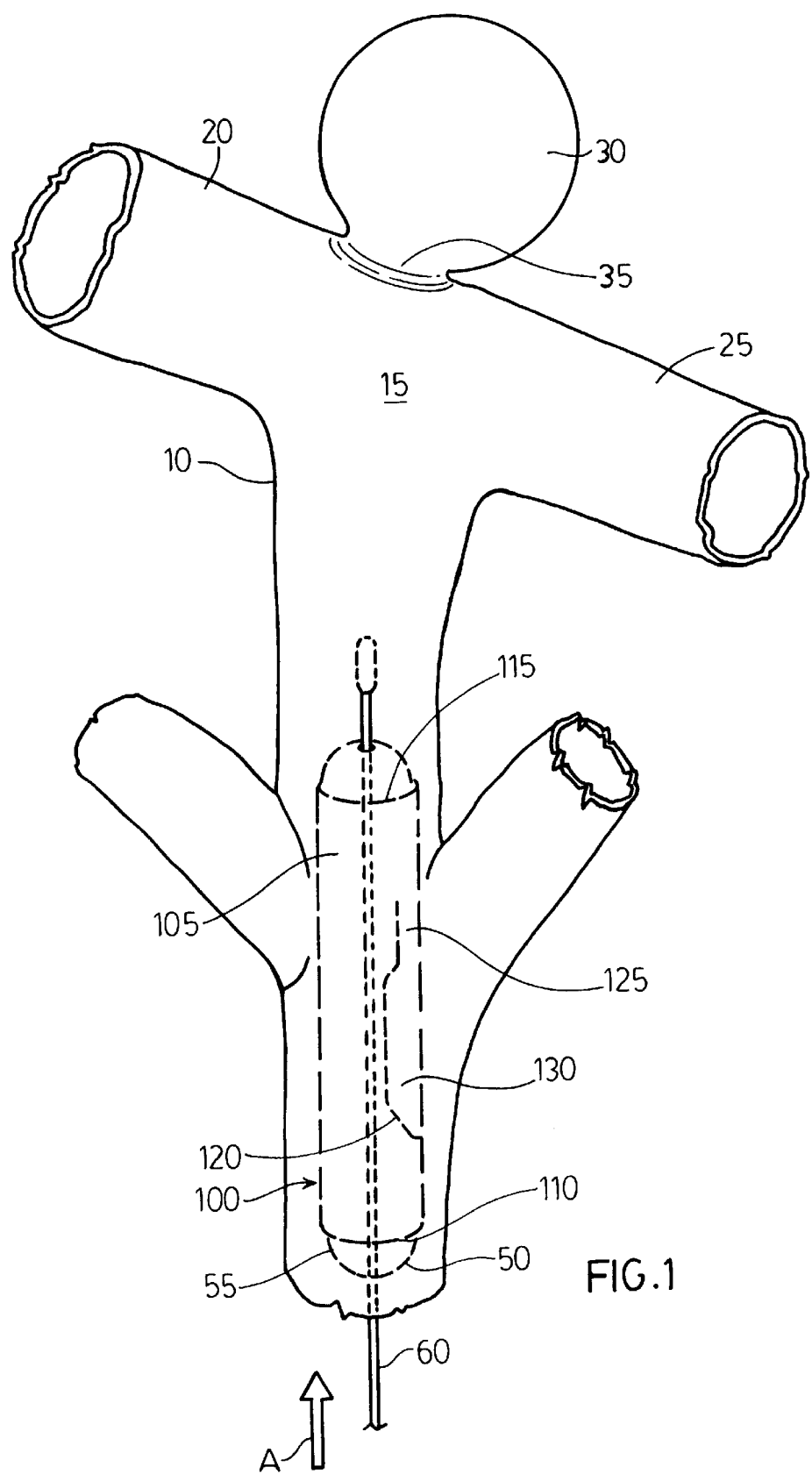
FIGS. 1–5 illustrate a perspective view, partially cut away, of the terminal bifurcation of the basilar artery into which the a first embodiment of the present endovascular prosthesis is being delivered and implanted.

With reference to FIGS. 1–5, a first embodiment of the present endovascular prosthesis will be described with particular reference to implantation of same at the terminal bifurcation of the basilar artery.

Thus there is illustrated a basilar artery 10 which terminates at a junction 15 which bifurcates into pair of secondary arteries 20,25. Located at junction 15 is an aneurysm 30. Aneurysm 30 has an opening 35 (shown enlarged for illustrative purposes only) through blood enters and sustains aneurysm 30.

An endovascular prosthesis 100 is mounted on a catheter 50.

Catheter 50 comprises an inflatable balloon 55 and a guidewire 60. Catheter 50, inflatable balloon 55 and guidewire 60 are conventional. As is known in the art, inflatable balloon 55 is moveable along guidewire 60.

Endovascular prosthesis 100 is constructed of a body 105. Body 105 comprises a proximal end 110 and a distal end 115. Endovascular prosthesis 100 further comprises a leaf portion 120 attached to body 105. As illustrated, leaf portion comprises a neck 125 and a head 130. Head 130 is wider than neck 125. In the illustrated embodiment, head 130 of leaf portion 120 points away from distal end 115 (i.e., head 130 of leaf portion 120 points toward proximal end 110).

Body 105 is a generally tubular element and should be constructed to be sufficiently flexible such that it can be navigated to the target body passageway yet be sufficiently expandable such that it can be fixed at the proper location in target body passageway.

One approach to achieve this is to construct endovascular prosthesis 100 from a structure resembling a stent. As is known in the art, a stent is an expandable prosthesis which is generally used to obtain and maintain the patency of a body passageway (e.g., blood vessels, respiratory ducts, gastrointestinal ducts and the like). The two general design requirements of a stent are: (i) it must be sufficiently flexible in the unexpanded state such that it may be navigated to the target body passageway intact, and (ii) it must be sufficiently radially rigid in the expanded state to avoid the occurrence of restenosis and/or stent recoil. The present endovascular prosthesis is not a stent, per se, since design requirement (ii) need not be met—i.e., the aim of the present endovascular prosthesis is not to maintain patency of blocked body passageway. Rather, the present endovascular prosthesis comprises one or more expandable elements for the purposes of securing the prosthesis in the correct position.

Thus, in this approach body 105 may be a porous tube having a porosity defined by a plurality of intersecting members (for clarity, the porosity of body 105 is not illustrated in FIGS 1–5). The precise pattern of the intersecting members is not particularly restricted and should be chosen to achieve sufficient flexibility of the porous tube in the unexpanded state while having the potential to achieve at least some degree of expansion with radially outward forces on the tube. Typically, the plurality of intersecting members will be arranged to define a regular repeating pattern. See, for example, the various repeating patterns disclosed in the following copending patent applications:

Canadian patent application number 2,134,997 (filed Nov. 3, 1994);

Canadian patent application number 2,171,047 (filed Mar. 5, 1996);

Canadian patent application number 2,175,722 (filed May 3, 1996);

Canadian patent application number 2,185,740 (filed Sep. 17, 1996);

Canadian patent application number 2,192,520 (Dec. 10, 1996);

International patent application PCT/CA97/00151 (filed Mar. 5, 1997);

International patent application PCT/CA97/00152 (filed Mar. 5, 1997); and

International patent application PCT/CA97/00294 (filed May 2, 1997);

the contents of each of which are hereby incorporated by reference (hereinafter collectively referred to as the "Divysio patent applications") and the various references cited therein. While the repeating patterns disclosed in the in the Divysio patent applications are suited for use in stent designs, they may be modified to increase the flexibility of the tubular structure (e.g., by altering the polygonal design taught in the Divysio patent application applications) to be useful in the present endovascular prosthesis notwithstanding that the resultant tube may not be useful as a stent.

Body 105 may be constructed of any suitable material. In one preferred embodiment, body 105 is constructed of a plastically deformable material such as a metal, alloy or polymer. Non-limiting examples of suitable metals and alloys may be selected from the group comprising stainless steel, titanium, tantalum and the like. In this embodiment, the radially outward force used to expand body 105 may be applied by expansion of a catheter-mounted balloon, as will be discussed in more detail hereinbelow. In another preferred embodiment, body 105 is constructed of "shape memory" metal alloy (e.g., nitinol) capable of self-expansion at a temperature of at least about 30° C., preferably in the range of from about 30° to about 40° C. In this embodiment, it will be appreciated that an inherent radially outward force causes expansion of body 105 when it is exposed to an environment at the programmed self-expansion temperature. In yet another preferred embodiment, body 105 may be construct of a biodegradable material. As is known in the art, a biodegradable material will degrade upon prolonged contact with body fluids and would be useful in the present endovascular prosthesis since aneurysm obliteration may occur within minutes after closing of the aneurysmal opening.

The manner by which body 105 is manufactured is not particularly restricted. Preferably, the body 105 is produced by laser cutting techniques applied to a tubular starting material. Thus, the starting material could be a thin tube of a metal, alloy or polymer as described above which would then have sections thereof cut out to leave the desired repeating pattern discussed above. By using such a technique, it is then possible to produce leaf portion 120 simply by laser machining a cut in the outline of neck 125 and head 130 of leaf portion 120.

Alternatively, it is possible to construct body 105 having the desired porous repeating pattern from one or more pre-formed wires. In another alternate embodiment, it is possible to construct body 105 having the desired porous repeating pattern using a flat bed laser cutting technique, optionally combined was a welding technique.

Since endovascular prosthesis 100 functions by blocking opening 35 to aneurysm 30, it is important that leaf portion 120 be designed accordingly. Specifically, leaf portion 120 should be design such that it may occlude opening 35 to aneurysm 30. This may be achieved in a number of ways. In one embodiment, head 130 of leaf portion 120 is designed to be non-porous. In another embodiment, head 130 of leaf portion 120 is designed to be porous (e.g., for ease of manufacture of body 105) and thereafter covered with a suitable non-porous coating material. The non-porous coating material may be active (e.g., a pharmaceutical, an adhesive and the like to a non-porous surface and an additional benefit) or inactive (e.g., an inert coating material which serves the sole purpose of providing a non-porous surface). In yet another embodiment, the entire surface of leaf portion 120 (i.e., the combination of neck 125 and head 130) may be non-porous by original design or originally porous and subsequently covered with a non-porous coating.

Endovascular prosthesis 100 may further comprise a coating material thereon. The coating material may be disposed continuously or discontinuously on the surface of the prosthesis. Further, the coating may be disposed on the interior and/or the exterior surface(s) of the prosthesis. The coating material can be one or more of a biologically inert material (e.g., to reduce the thrombogenicity of the prosthesis), a medicinal composition which leaches into the wall of the body passageway after implantation (e.g., to provide anticoagulant action, to deliver a pharmaceutical to the body passageway and the like) and the like.

Endovascular prosthesis 100 is preferably provided with a biocompatible coating in order to minimize adverse interaction with the walls of the body vessel and/or with the liquid, usually blood, flowing through the vessel. The coating is preferably a polymeric material, which is generally provided by applying to the prosthesis a solution or dispersion of preformed polymer in a solvent and removing the solvent. Non-polymeric coating material may alternatively be used. Suitable coating materials, for instance polymers, may be polytetraflouroethylene or silicone rubbers, or polyurethanes which are known to be biocompatible. Preferably, however, the polymer has zwitterionic pendant groups, generally ammonium phosphate ester groups, for instance phosphoryl choline groups or analogues thereof. Examples of suitable polymers are described in International application numbers WO-A-93/16479 and WO-A-93/15775. Polymers described in those specifications are hemo-compatible as well as generally biocompatible and, in addition, are lubricious. It is important to ensure that the surfaces of the prosthesis are completely coated in order to minimize unfavourable interactions, for instance with blood, which might lead to thrombosis in the parent vessel.

This good coating can be achieved by suitable selection of coating conditions, such as coating solution viscosity, coating technique and/or solvent removal step.

With further reference to FIG. 1, once it is desired to implant endovascular prosthesis 100, it is mounted on balloon 55 of catheter 50. Catheter 50 is then translated through basilar artery 10 in the direction of arrow A.

Figure 2:
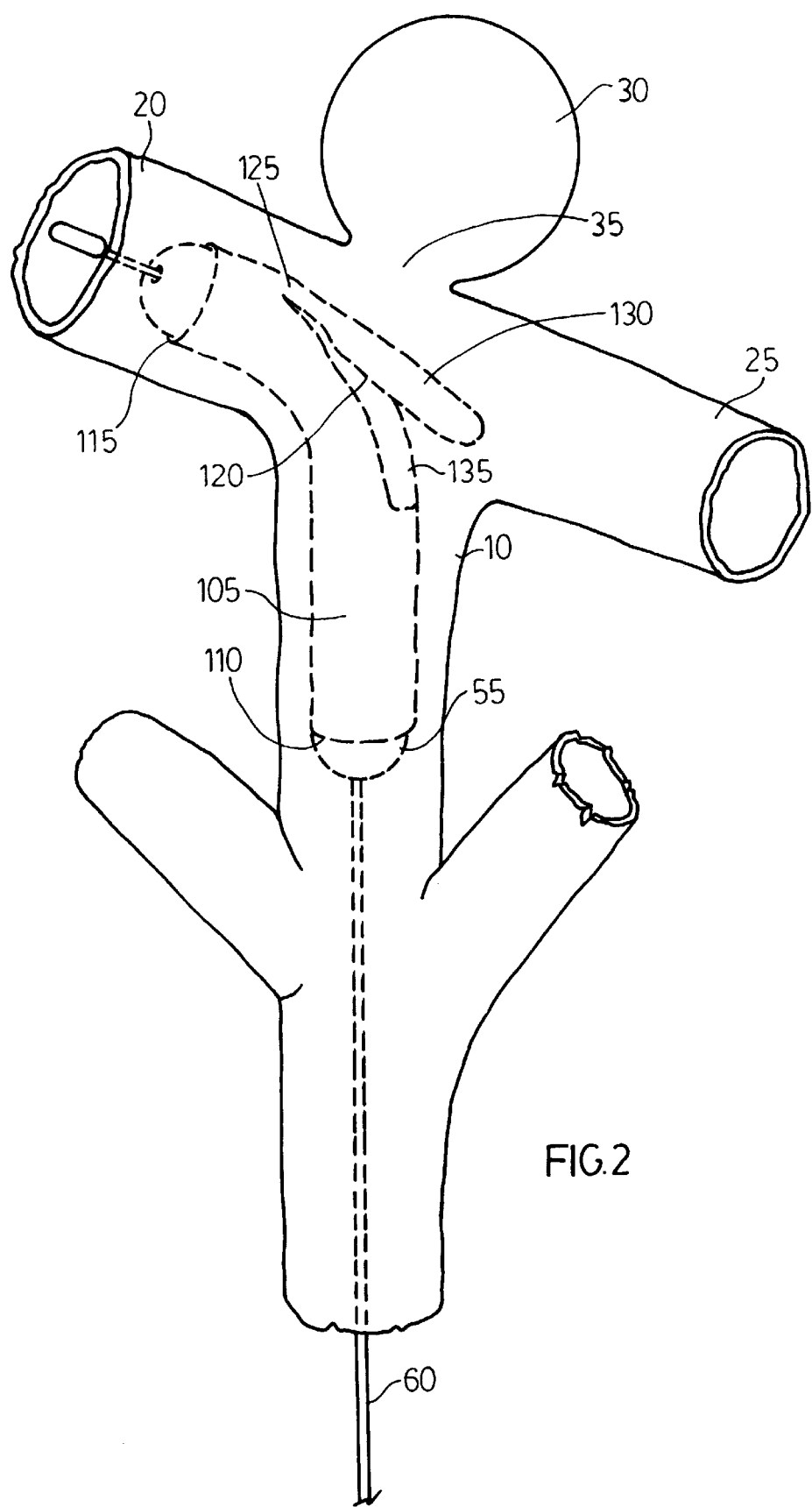

With reference to FIG. 2, endovascular prosthesis 100 mounted on balloon 55 of catheter 50 is navigated to the location of aneurysm 30 using conventional guidewire and fluoroscopy techniques. In the illustrated embodiment, distal end 115 of body 105 enters secondary artery 20. In practice, the secondary arteries at the bifurcation of the basilar artery are asymmetric and distal end 115 of body 105 is navigated into the larger of the two secondary arteries. Further, in the illustrated embodiment, as body 105 is flexed on navigation into secondary artery 20, leaf portion 120 lifts or moves out of alignment with respect to the tubular plane of body 105 to define an opening 135.

Figure 3:
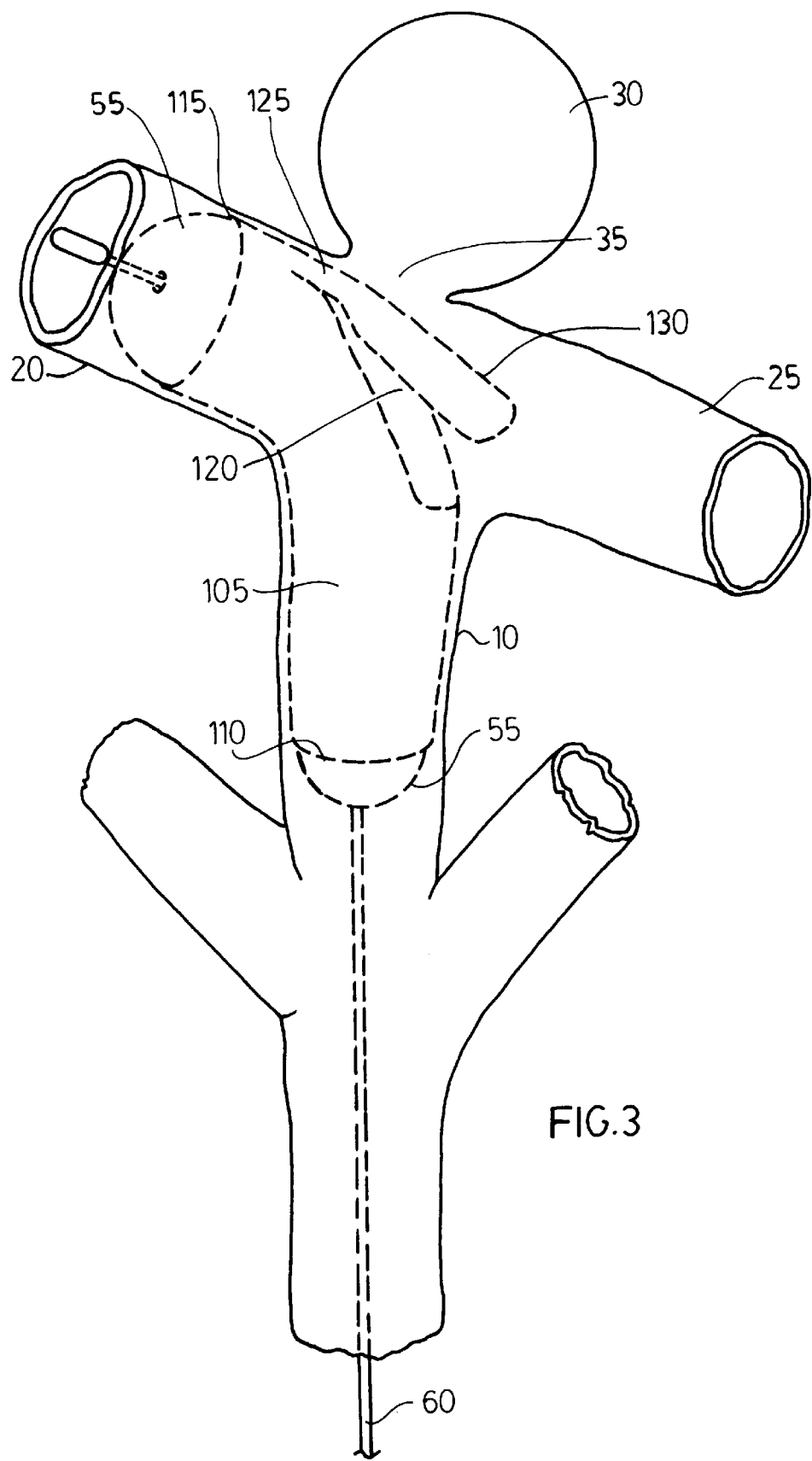
Figure 4:
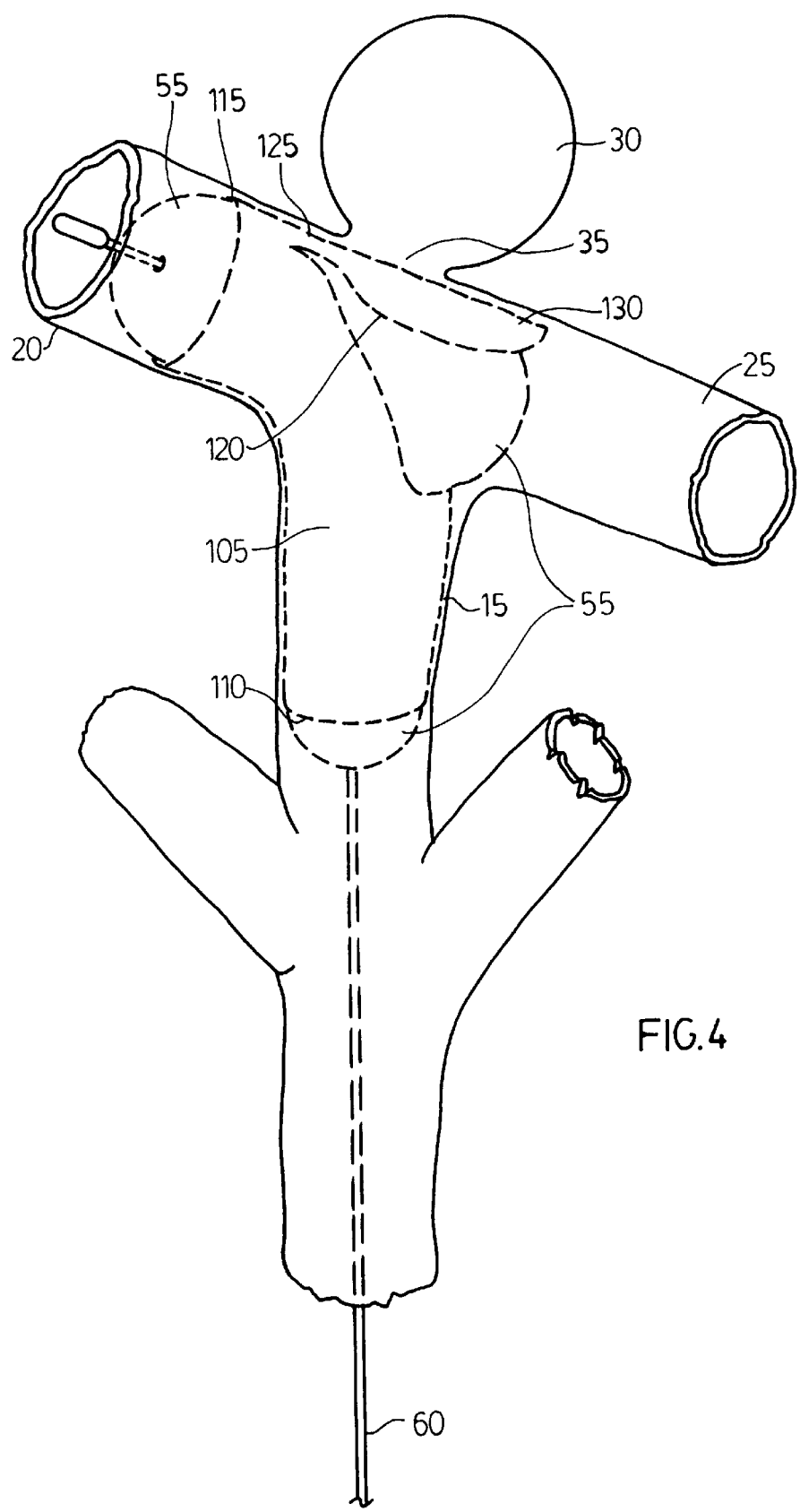

With reference to FIGS. 3 and 4, once endovascular prosthesis 100 is in the correct position, balloon 55 is expanded thereby exerting radially outward forces on body 105. Initially, this results in expansion of body 105 such that a portion of it is urged against the walls of both of basilar artery 10 and secondary artery 20. With reference to FIG. 4, as expansion of balloon 55 continues, a portion of balloon 55 urges against neck 125 and head 130 of leaf portion 120 resulting in urging of leaf portion 120 against the walls of secondary arteries 20,25 in a manner which results in blocking of opening 35 of aneurysm 30.

Figure 5:
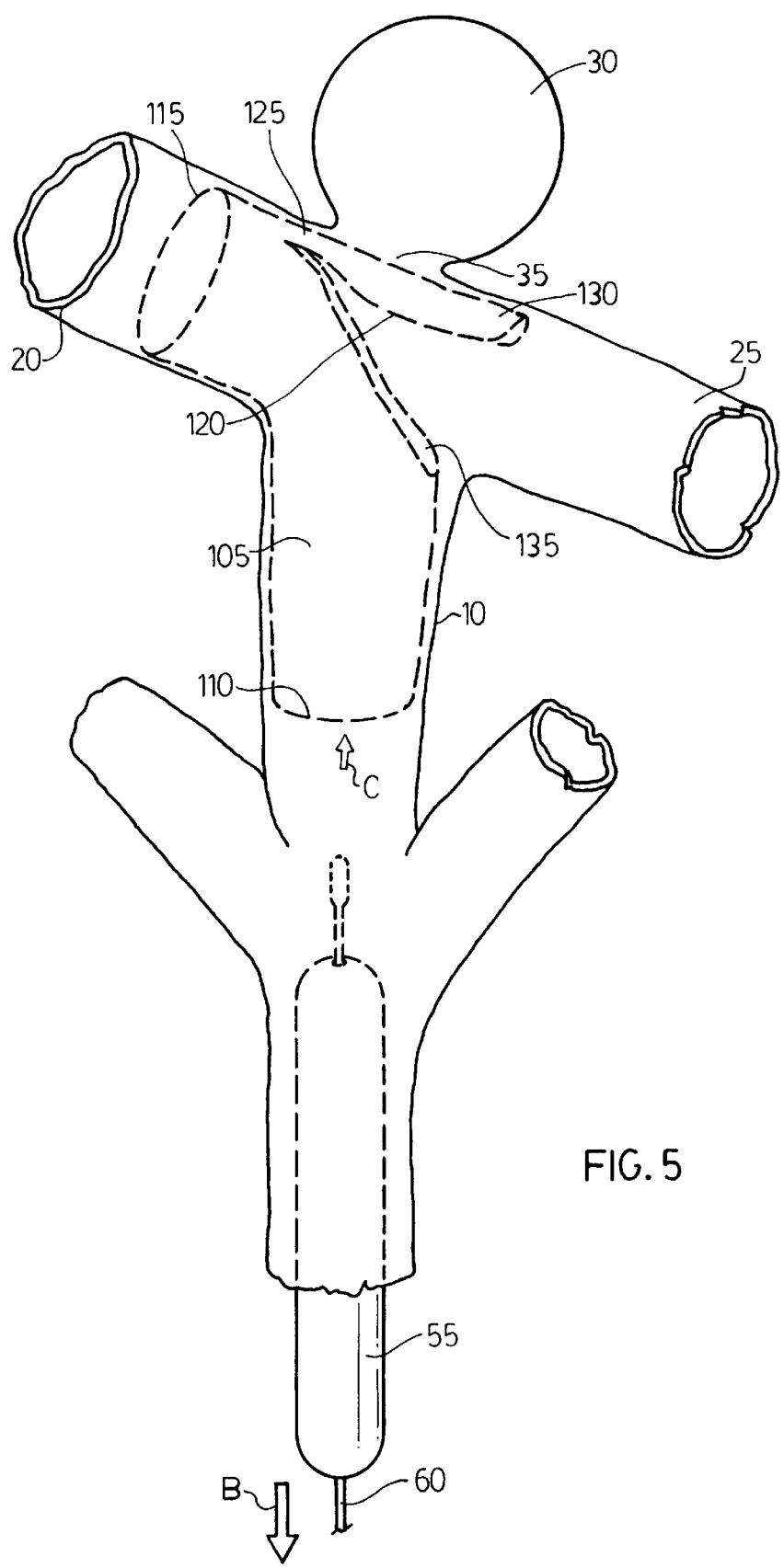

With reference to FIG. 5, balloon 55 is deflated and, together with guidewire 60, withdrawn from endovascular prosthesis 100 in the direction of arrow B. In the illustrated embodiment, endovascular prosthesis 100 is secured in position by body 105 being urged against the walls of basilar artery 10 and secondary artery 20. Further, in the illustrated embodiment, leaf portion 120 is secured in position by a combination forces against it by the flow of the blood in the direction of arrow C and the inherent forces open flexure of body 105 to navigate distal end 115 into secondary artery 20. Once leaf portion 120 blocks opening 35, aneurysm 30 is obliterated thereafter.

Figure 6:
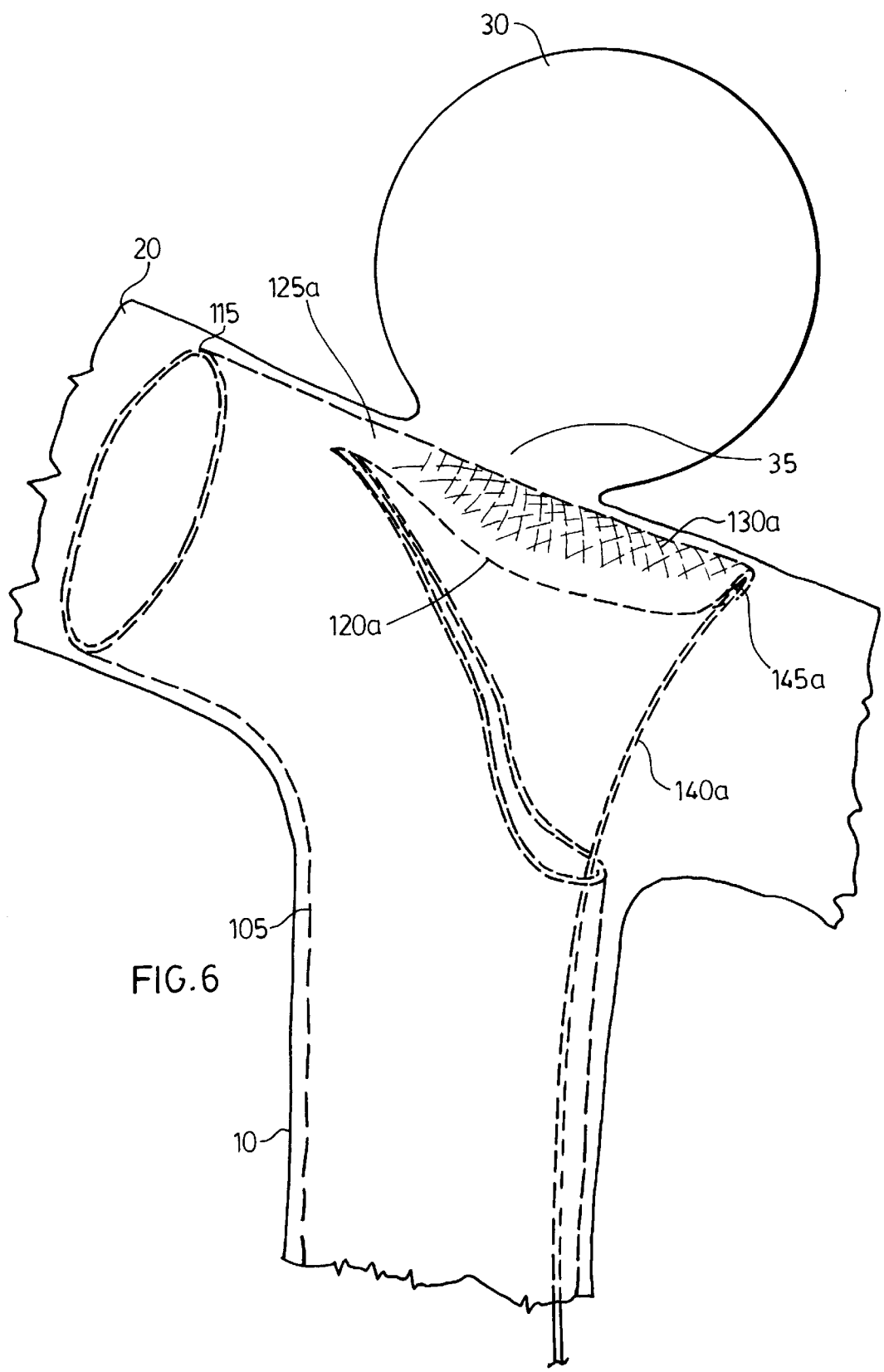
FIG. 6 illustrates an enlarged view of a modification to the first embodiment of the present endovascular prosthesis illustrated in FIGS. 1–5.

With reference to FIG. 6, there is illustrated an enlarged view of a modification to the endovascular prosthesis illustrated in FIGS. 1–5. In FIG. 6, like numerals are used to designate like elements in FIGS. 1–5 and modified or new elements in FIG. 6 are denoted with the suffix "a". Specifically, leaf portion 120a has been modified such that neck 125a is made of an electrically non-conductive material whereas head 130a is made of an electrically conductive material. Additionally, a pharmaceutically acceptable adhesive 132a is disposed on the aneurysmal side of head 130a and a positioning wire 140a is secured to head 130a at a connection point 145a. In use, positioning wire 140a may be utilized to orient leaf portion 120a such that head 130a correctly closes opening 35 of aneurysm 30. Once leaf portion 120a is in the correct position, an electric current is passed through positioning wire 140a thereby resulting in detachment thereof from head 130a at connection point 145a. Additionally, depending on the nature of adhesive 132a, the electric current which is passed through positioning wire 140a may serve the additional purpose of activating adhesive 132a. Of course, it is possible to modify the specific embodiment illustrated in FIG. 6, for example, to: (i) omit adhesive 132a so that the electric current serves to seal head 130a to the periphery of opening 35; (ii) omit positioning wire 140a so that the seal of head 130a to the periphery of opening is achieved via adhesive 132a; or (iii) to construct head 130a from the same material (electrically conductive or non-conductive) so that the principal purpose of positioning wire 140a is alignment of leaf portion 120a.

A preferred modification to the embodiments illustrated in FIGS. 1–6 involves modifying positioning wire 140a to a supplementary (or second) guidewire to guidewire 60 illustrated in FIGS. 1–5. Specifically, whereas guidewire 60 is navigated in secondary artery 20, the supplementary guidewire would pass through an aperture in the leaf portion (e.g., near the location of connection point 145a in FIG. 6) and be navigated into secondary artery 25 during implantation of the endovascular prosthesis. By passing the supplementary guidewire through the leaf portion in this fashion, delivery of the prosthesis is greatly facilitated and, importantly, enhanced control is achieved of the orientation of the leaf portion to seal the aneurysmal opening.

Figure 7:
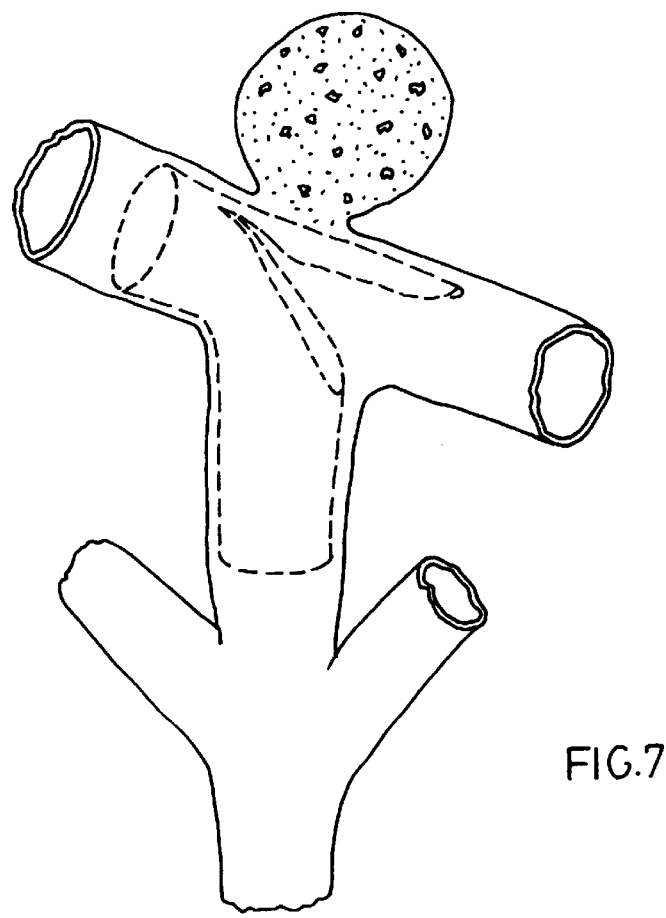
FIG. 7 illustrates an enlarged view of another modification to the first embodiment of the present endovascular prosthesis illustrated in FIGS. 1–5.

With reference to FIG. 7, there is illustrated yet another modification to the endovascular prosthesis illustrated in FIGS. 1–5. In FIG. 7, like numerals are used to designate like elements in FIGS. 1–5 and modified or new elements in FIG. 7 are denoted with the suffix "b". Specifically, leaf portion 120b has been modified such that head 130b is coated on the aneurysmal side thereof with a pharmaceutically acceptable expandable compound 132b. In use, once leaf portion 120b is orientated such that head 130b correctly closes opening 35 of aneurysm 30, expandable compound 132b chemically reacts with bodily fluids expands to fill aneurysm 30 as an expanded compound 134b. Alternatively, expandable compound 132b may be electrically activated using a positioning wire such as illustrated in FIG. 6.

Figure 8:
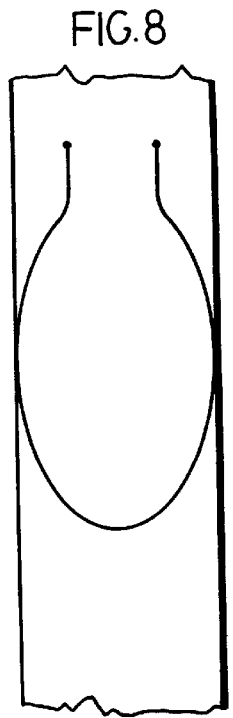
FIGS. 8–10 illustrate various embodiments of the shape of the leaf portion of the present endovascular prosthesis.
Figure 9:
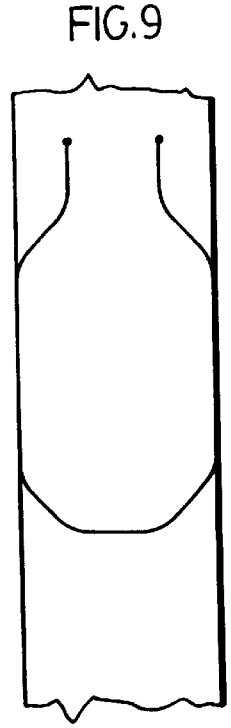
Figure 10:
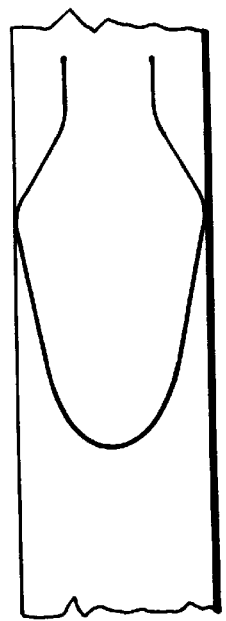

With reference to FIGS. 8–10, there are illustrated various modifications to the shape of the head of the leaf portion. In FIGS. 8–10, like numerals are used to designate like elements in FIGS. 1–5 and modified elements in FIGS. 8–10 are denoted with the suffix "c", "d" and "e", respectively. It will be clear to those of skill in the art that head 130c, 130d or 130e illustrated in FIGS. 8–10, respectively, may be cut out of or overlap with respect to body 105.

Figure 11:
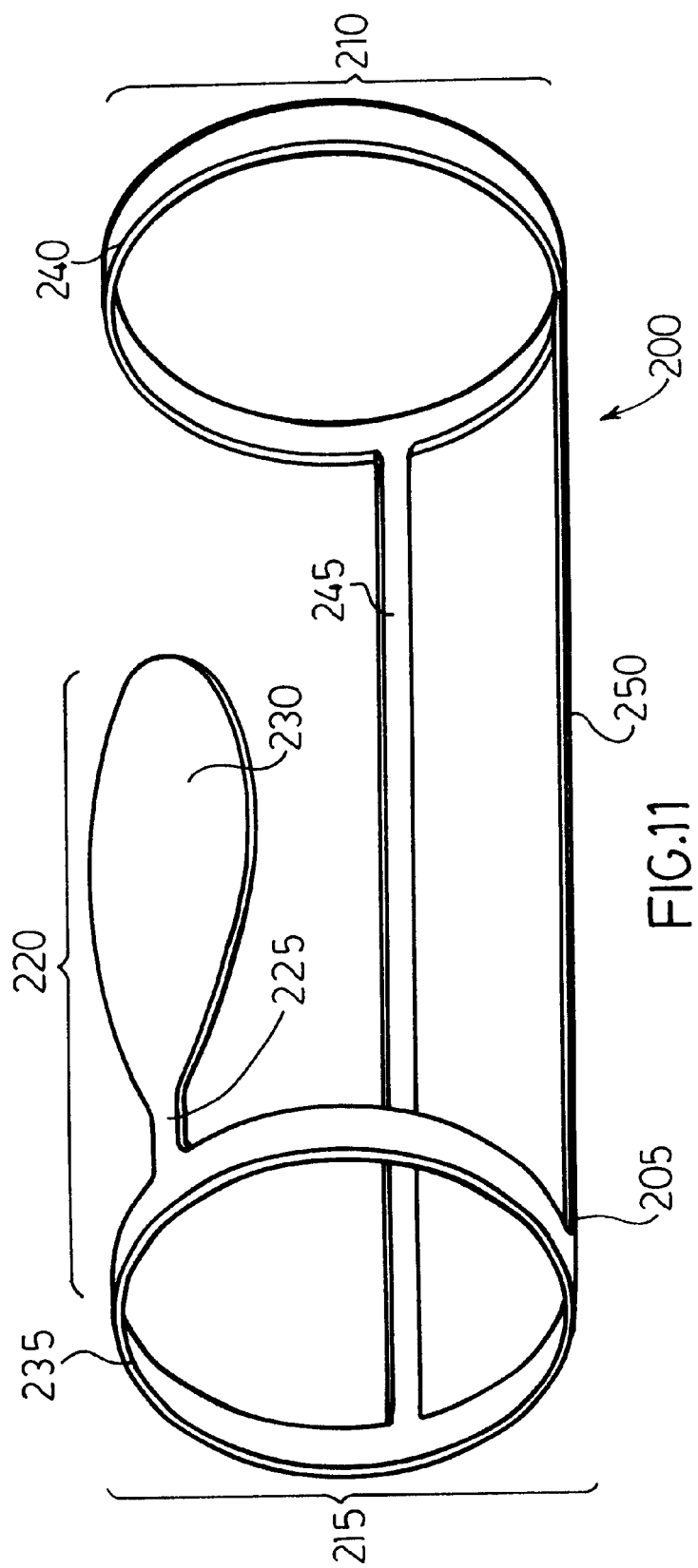
FIG. 11 illustrates a perspective view of a second embodiment of the present endovascular prosthesis.
Figure 12:
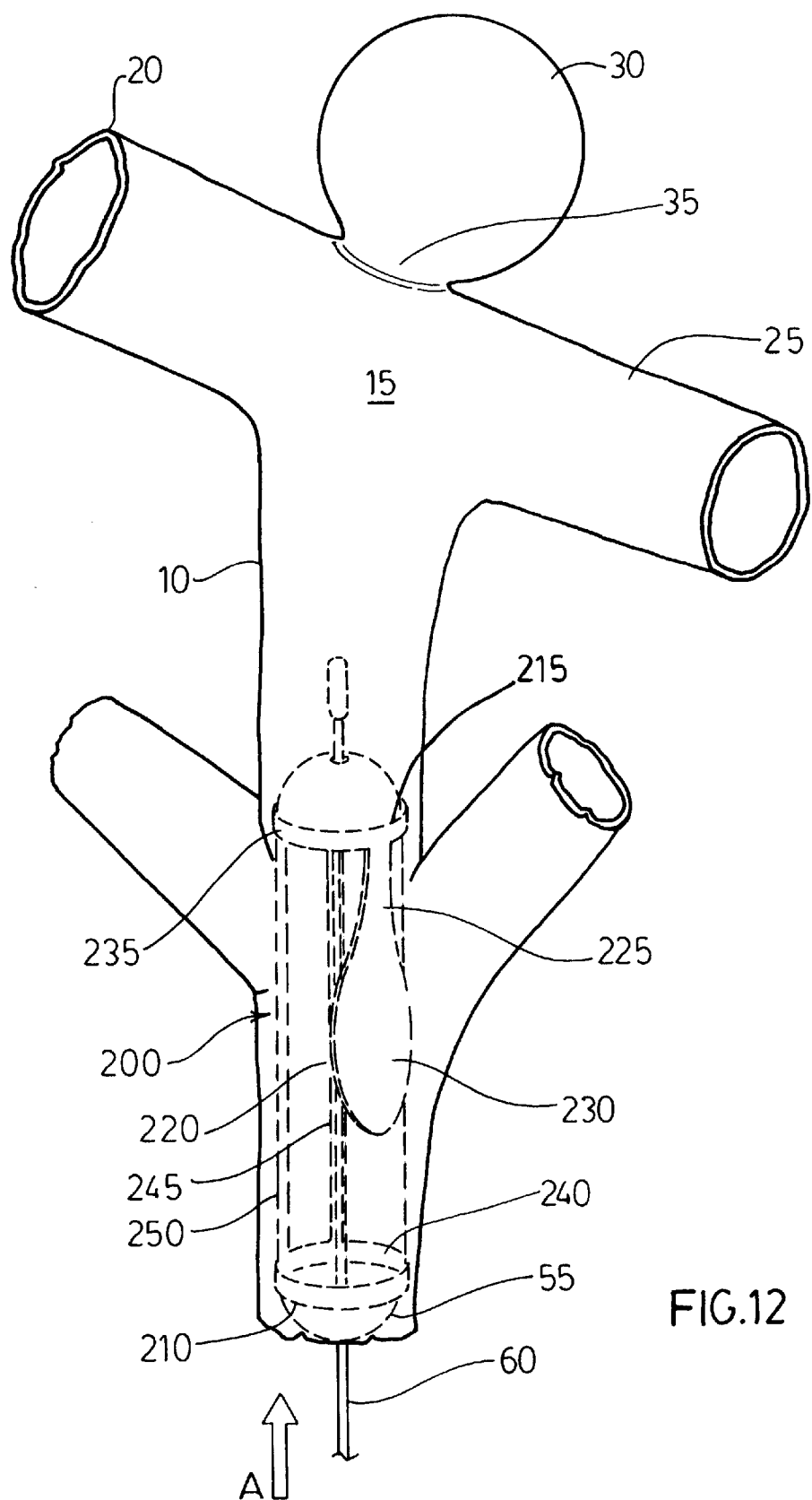
FIGS. 12–15 illustrate a perspective view, partially cut away, of the terminal bifurcation of the basilar artery into which the embodiment illustrated in FIG. 11 is being delivered and implanted.
Figure 13:
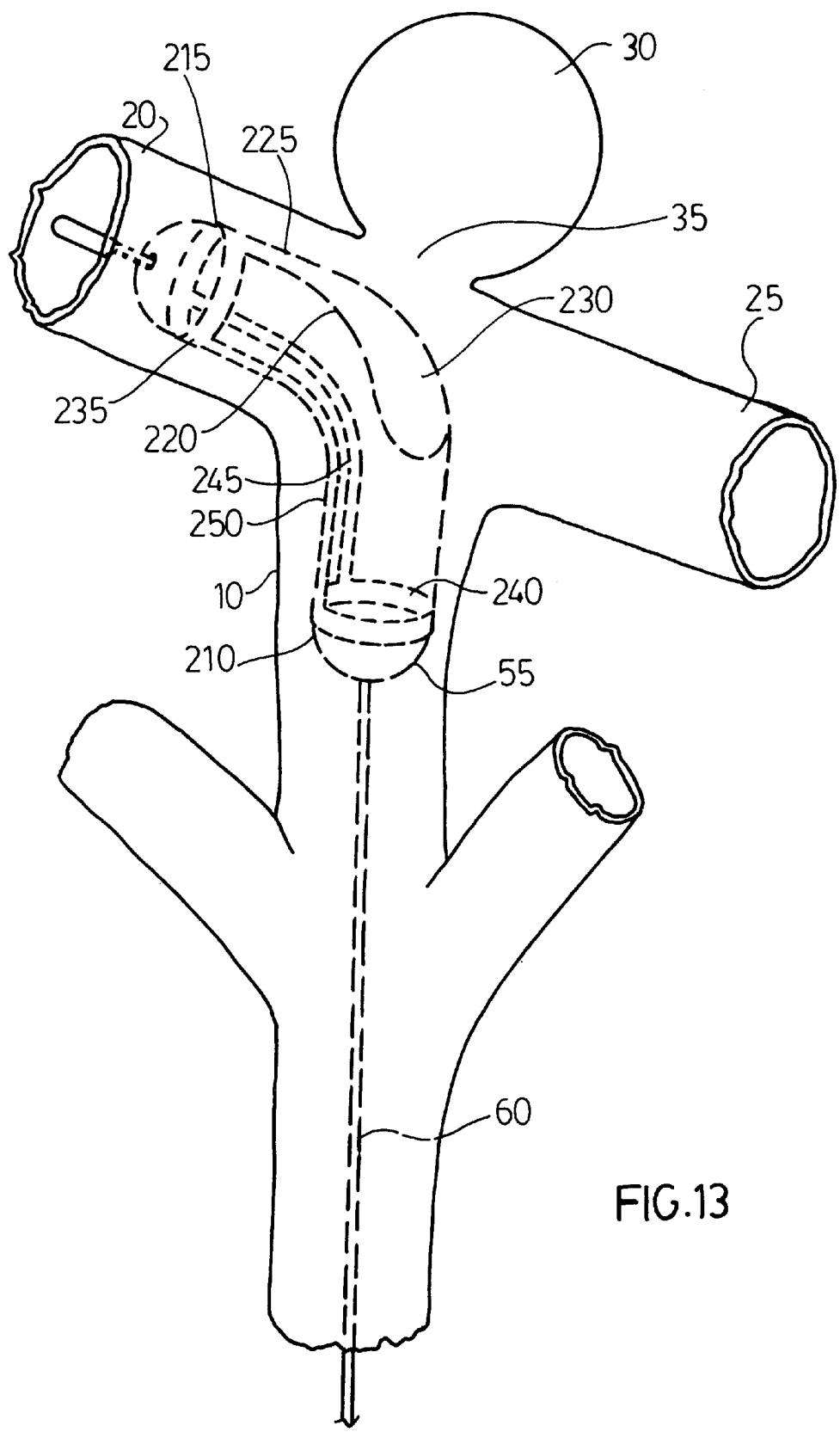
Figure 14:
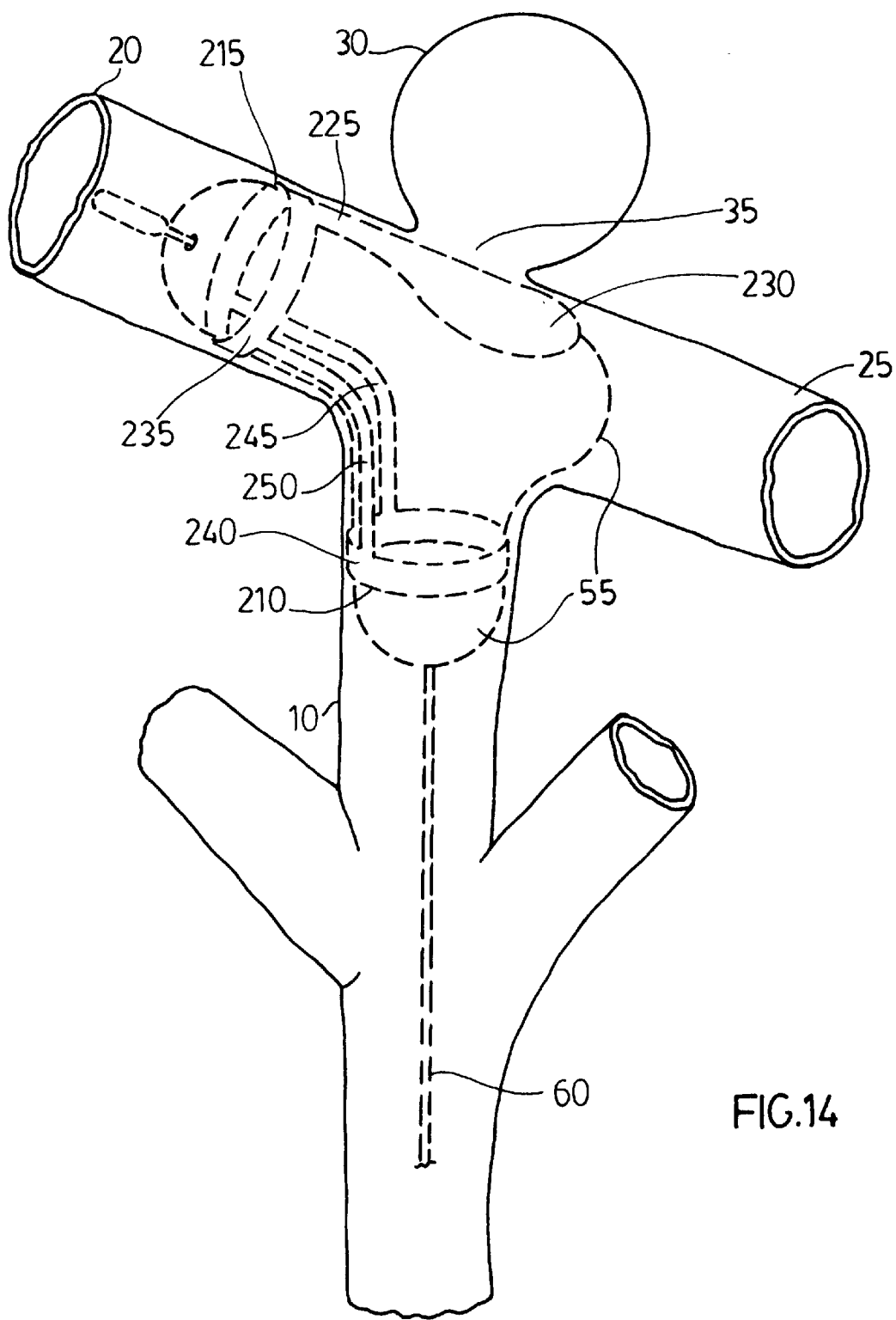
Figure 15:
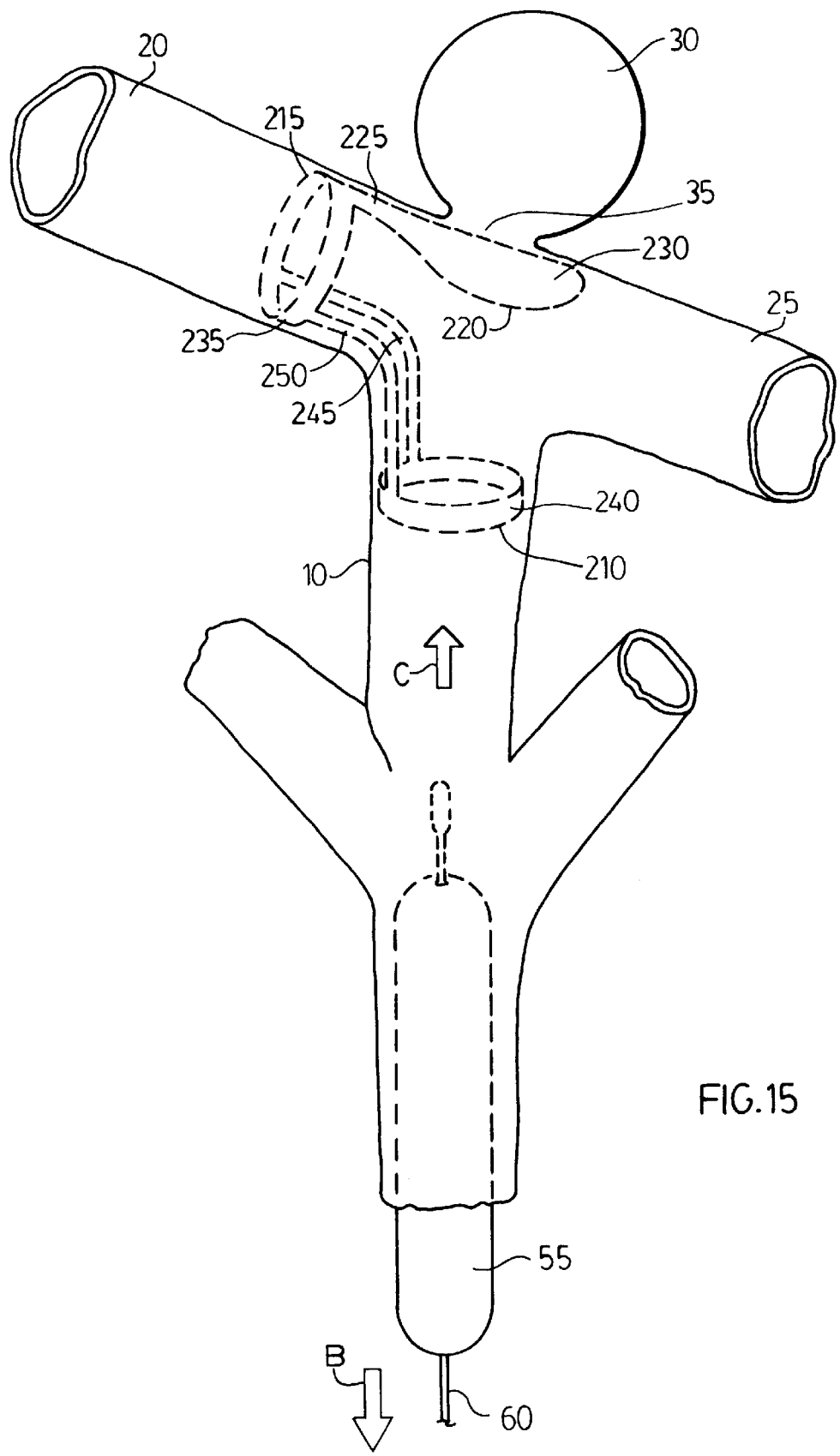

With reference to FIG. 11 there is illustrated a second embodiment of the present invention in the form of endovascular prosthesis 200. Endovascular prosthesis 200 is constructed of a body 205. Body 205 comprises a proximal end 210 and a distal end 215. Endovascular prosthesis 200 further comprises a leaf portion 220 attached to body 205. As illustrated, leaf portion 220 comprises a neck 225 and a head 230. Head 230 is wider than neck 225. In the illustrated embodiment, head 230 of leaf portion 220 points away from distal end 215 (i.e., head 230 of leaf portion 220 points toward proximal end 210).

Body 205 further comprises a pair of rings 235,240 which are interconnected by a pair of wires 245,250. In the illustrated embodiment leaf portion 220 is connected to ring 235. Wires 245,250 preferably are dimensioned to confer to prosthesis 200 sufficient integrity while maximizing flexibility to provide enhanced navigation. The purpose of wires 245,250 is to interconnect rings 235,240 while allowing prosthesis 200 to be sufficiently flexible such that it can be navigated to the target body passageway yet be sufficiently expandable such that it can be fixed at the proper location in target body passageway. Wires 245,250 are not particularly important during expansion of prosthesis 200 (i.e., after the point in time at which prosthesis 200 is correctly positioned). Further, as will be apparent to those of skill in the art, leaf portion 220 is independently moveable with respect to proximal end 210 and distal end 215 of prosthesis 200 (in the illustrated embodiment, leaf portion 220 is independently moveable with respect to rings 235,240).

With reference to FIGS. 12–15, prosthesis 200 is mounted on a catheter 50 and delivered and implanted in the manner described above with reference to FIGS. 1–5. In this embodiment, it is preferred to implant prosthesis 200 in a manner such that wires 245,250 are adjacent basilar artery 10 and secondary artery 20 (in the illustrated embodiment).

This embodiment of the invention is useful in illustrating the difference between the present endovascular prosthesis and a conventional stent. Specifically, in this embodiment of the present prosthesis, the expansible elements are rings 235,240. Rings 235,240 comprise a porous structure of interconnecting struts which, for the purpose of clarity is not illustrated in the drawings. The precise nature of the porous structure of interconnecting struts is not particularly restricted and is within the purview of a person skilled in the art. The principal purpose of expanding rings 235,240 is to secure prosthesis 200 in place and not necessarily to alter the flow of blood through that portion of the artery in which the rings are expanded—i.e., this is the purpose of a stent.

Figure 16:
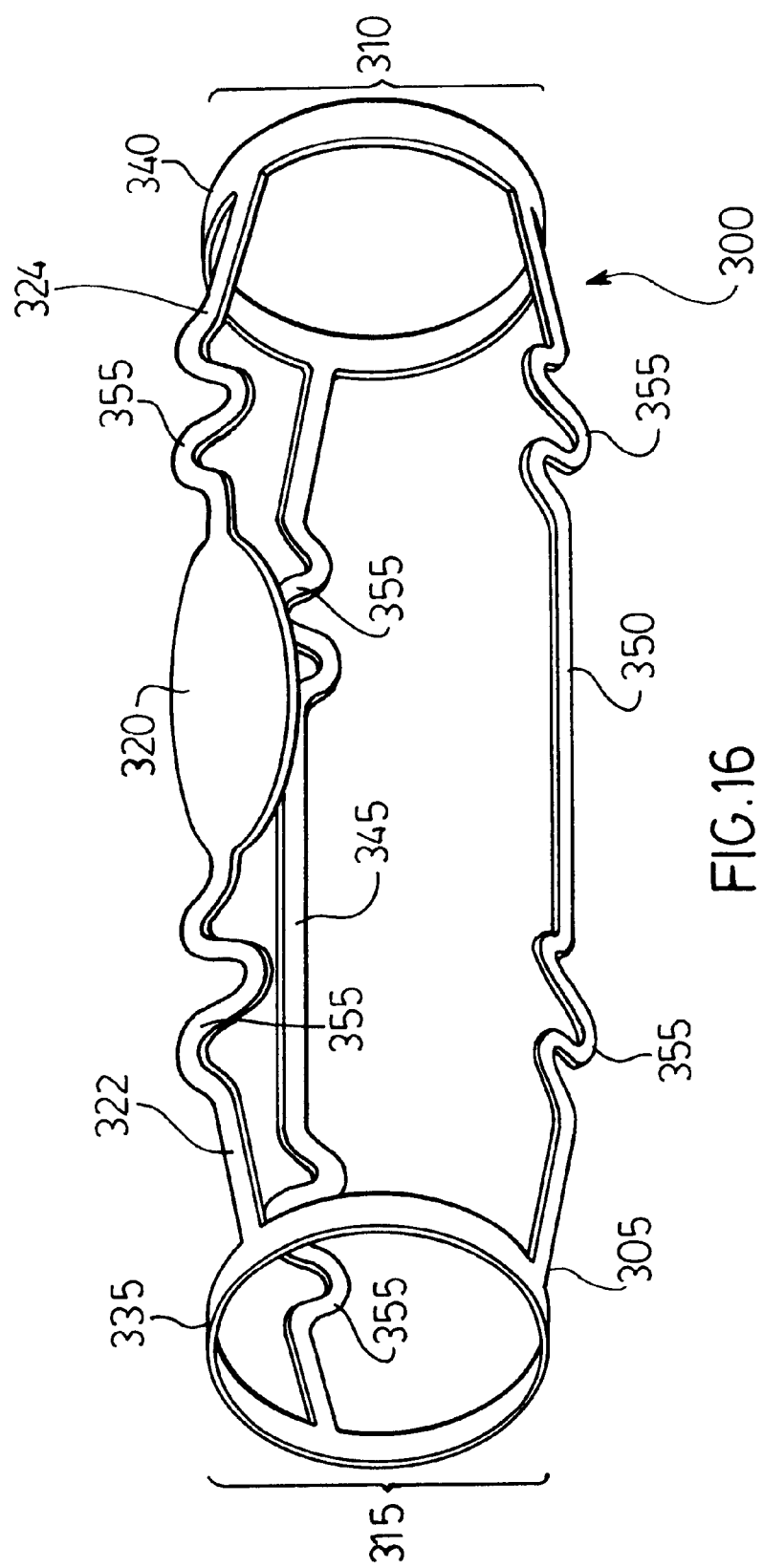
FIG. 16 illustrates a perspective view of a third embodiment of the present endovascular prosthesis.

With reference to FIG. 16 there is illustrated a third embodiment of the present invention in the form of endovascular prosthesis 300. Endovascular prosthesis 300 is constructed of a body 305. Body 305 comprises a proximal end 310 and a distal end 315. Endovascular prosthesis 300 further comprises a leaf portion 320 attached to body 305. Body 305 comprises a pair of rings 335,340 which are interconnected by a pair of wires 345,350. Again, rings 335,340 comprise a porous structure of interconnecting struts which, for the purpose of clarity is not illustrated in the drawings. The precise nature of the porous structure of interconnecting struts is not particularly restricted and is within the purview of a person skilled in the art. As illustrated, leaf portion 320 is connected to rings 335,340 by a pair of wires 322,324. Further, each of wires 345,350 each contains a pair of undulating sections 355, and each of wires 322,324 contains a single undulating section 355. Undulating section 355 improves flexibility and navigation of prosthesis 300.

Figure 17:
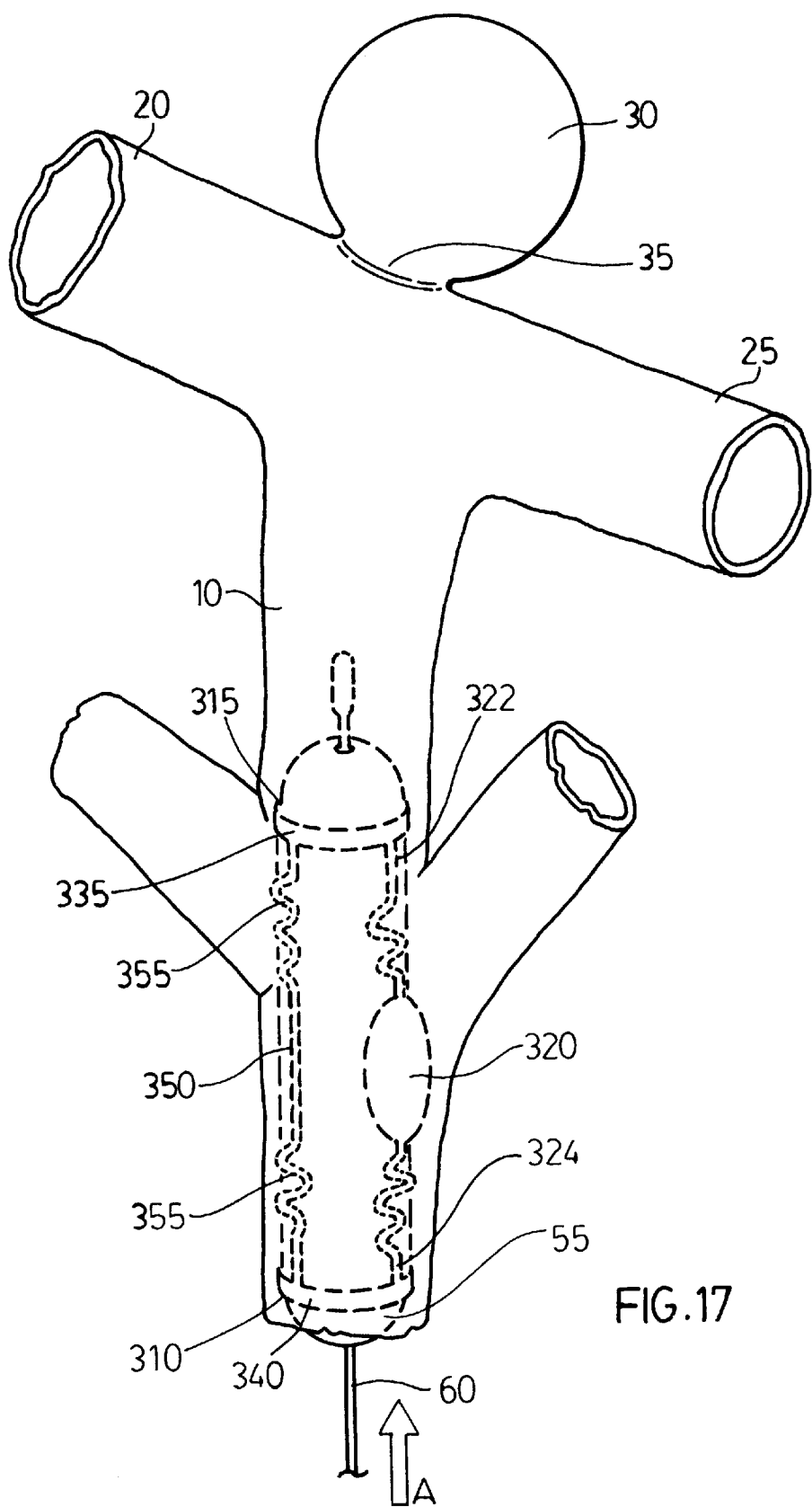
FIGS. 17–18 illustrate a perspective view, partially cut away, of the terminal bifurcation of the basilar artery into which the embodiment illustrated in FIG. 16 is being delivered and implanted.
Figure 18:
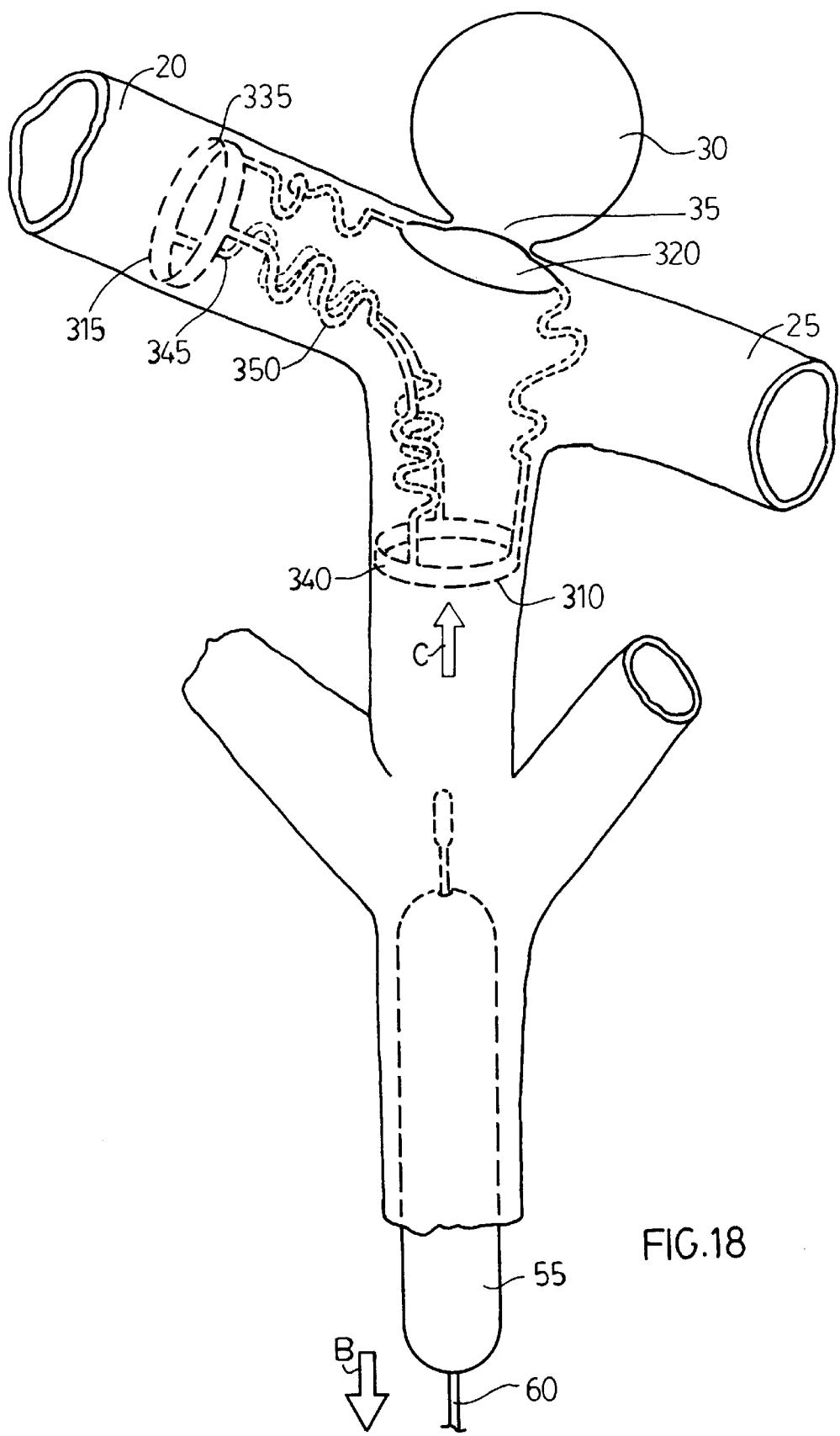

Again, wires 322,324,345,350 preferably are dimensioned to confer to prosthesis 300 sufficient integrity while maximizing flexibility to provide enhanced navigation. The purpose of wires 345,350 is to interconnect rings 335,340 while allowing prosthesis 300 to be sufficiently flexible such that it can be navigated to the target body passageway yet be sufficiently expandable such that it can be fixed at the proper location in target body passageway. Wires 345,350 are not particularly important during expansion of prosthesis 300 (i.e., after the point in time at which prosthesis 300 is correctly positioned). The purpose of wires 322,324 is to allow for more independent movement of leaf portion 230 with respect to proximal end 310 (in the illustrated embodiment this would in include ring 335) and distal end 315 (in the illustrated embodiment this would in include ring 340) of prosthesis 300. With reference to FIGS. 17–18, prosthesis 300 is mounted on a catheter 50 and delivered and implanted in the manner described above with reference to FIGS. 1–5. With further reference to FIG. 18, it will be appreciated by those of skill in the art that, for optimal effect, wires 322,324,345,350 should be positioned on rings 335,340 such that wire 324 does not cross secondary artery 25 after implantation of the endovascular prosthesis.

Figure 19:
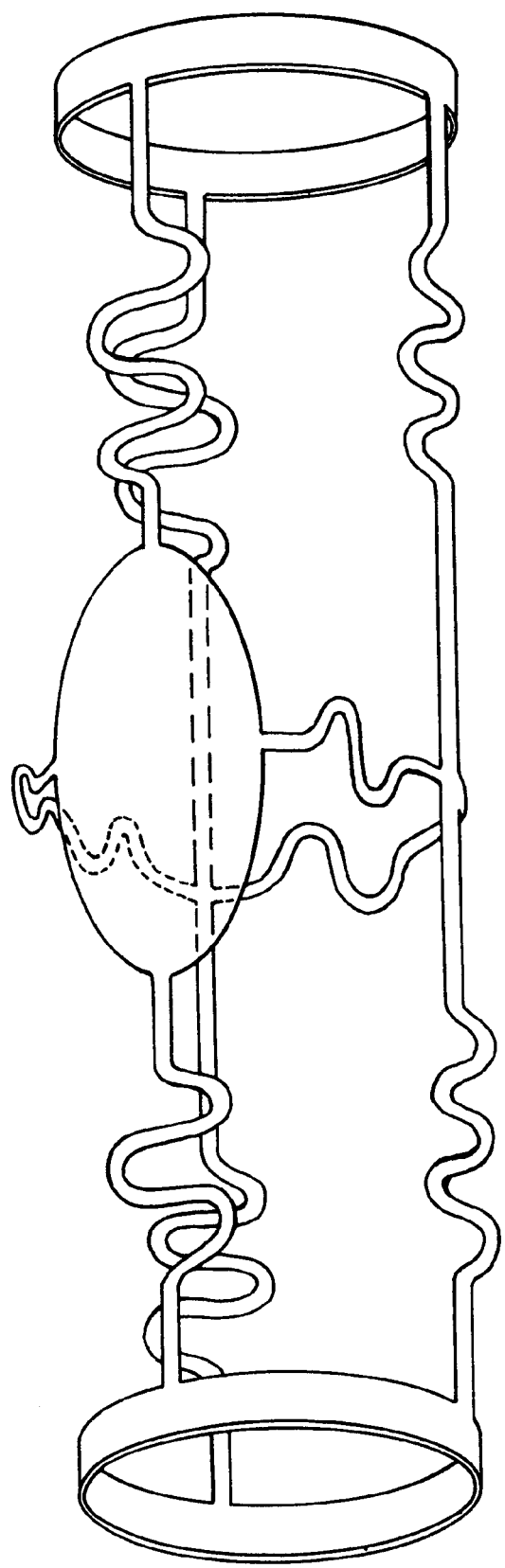
FIG. 19 illustrates an enlarged view of a modification to the embodiment of the present endovascular prosthesis illustrated in FIGS. 16–18.

With reference to FIG. 19, there is illustrated a modification to the endovascular prosthesis illustrated in FIGS. 16–18. In FIG. 19, like numerals are used to designate like elements in FIGS. 16–18 and new elements in FIG. 19 are denoted with the suffix "f". In FIG. 19, an undulating wire 326f has been added to interconnect leaf portion 320 and wires 345,350. Additionally, there is no interconnecting wire between leaf portion 320 and ring 340. In this embodiment, omission of an interconnecting wire between leaf portion 320 and ring 340 obviates a connecting wire crossing the lumen of secondary artery 25 after implantation of the endovascular prosthesis while addition of undulating wire 326f improves the physical integrity of the prosthesis.

Figure 20:
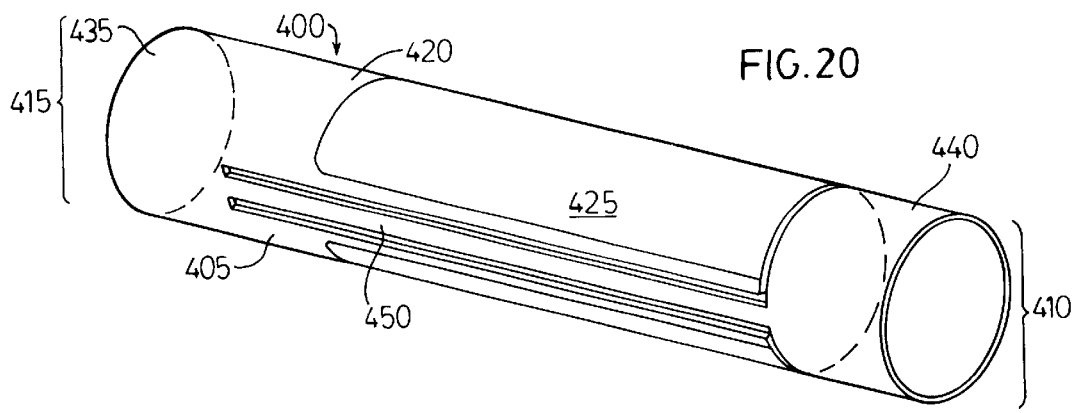
FIGS. 20–22 illustrate a perspective view of a preferred embodiment of the present endovascular prosthesis shown in schematic.
Figure 21:
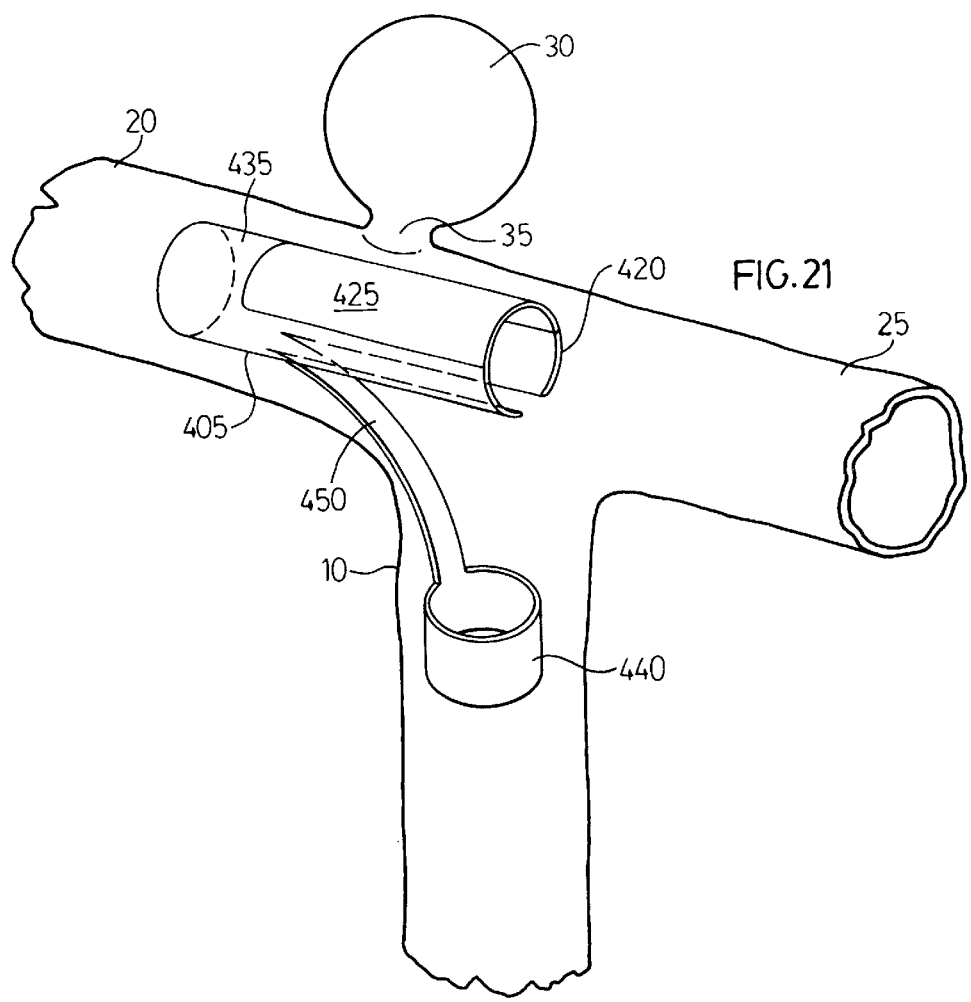
Figure 22:
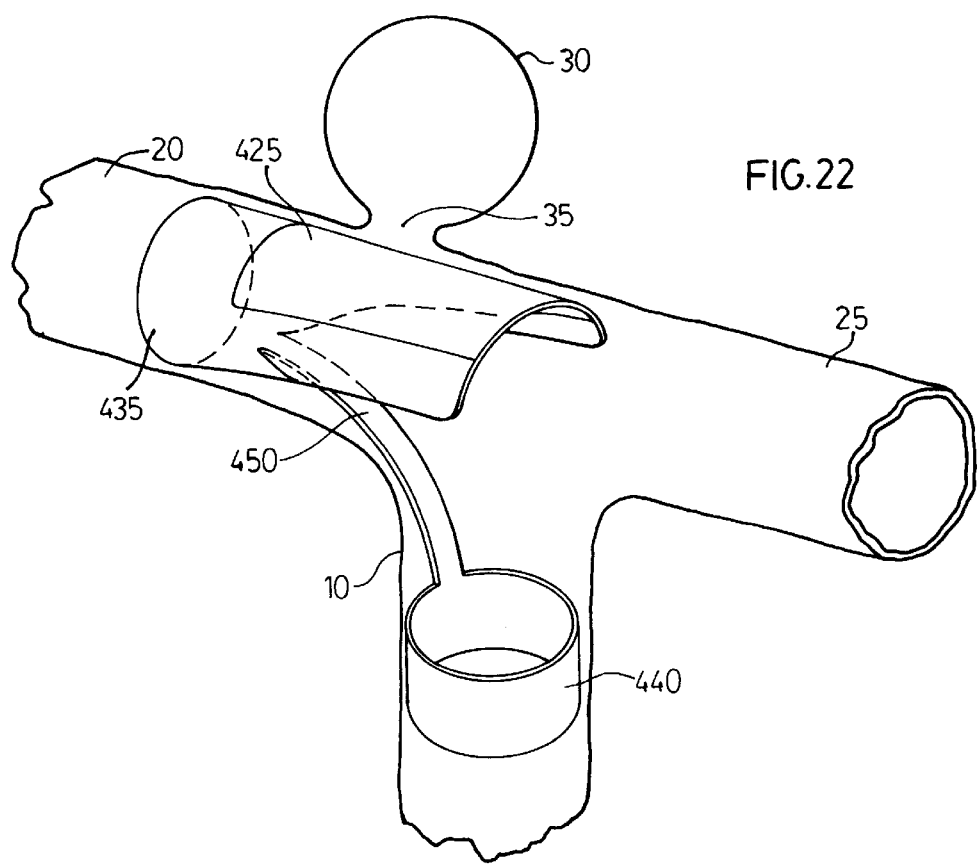

FIGS. 20–22 illustrate how the various elements of an endovascular prosthesis 400 may be cut out of a tubular starting material (again, for clarity, the specific porosity of prosthesis 400 and the balloon catheter delivery system are not illustrated in FIGS. 20–22).

Endovascular prosthesis 400 is constructed of a body 405. Body 405 comprises a proximal end 410 and a distal end 415. Endovascular prosthesis 400 further comprises a leaf portion 420 attached to body 405. As illustrated, leaf portion 420 comprises a blocking portion 425 for blocking aneurysmal opening 35. In the illustrated embodiment, the free end of leaf portion 420 points away from distal end 415 (i.e., the free end of leaf portion 420 points toward proximal end 410).

Body 405 further comprises a pair of expandable tubular sections 435,440 which are interconnected by a spine 450. In the illustrated embodiment leaf portion 420 is connected to tubular section 435. Spine 450 is preferably dimensioned to confer to prosthesis 400 sufficient integrity while maximizing flexibility to provide enhanced navigation. The purpose of spine 450 is to interconnect tubular sections 435,440 while allowing prosthesis 400 to be sufficiently flexible such that it can be navigated to the target body passageway. As will be apparent to those of skill in the art, leaf portion 420 is independently moveable with respect to proximal end 410 and distal end 415 of prosthesis 400 (in the illustrated embodiment, leaf portion 420 is independently moveable with respect to tubular sections 435,440).

Figure 23:
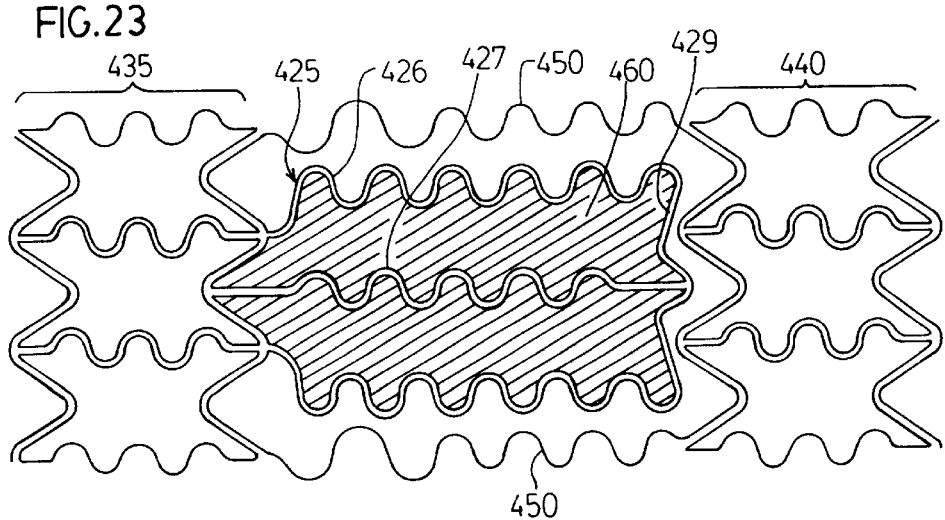
FIG. 23 illustrates an enlarged two-dimensional representation of one embodiment encompassed by the endovascular prosthesis illustrated in FIGS. 20–22.

FIG. 23 illustrates a two-dimensional representation of one embodiment of expandible prosthesis 400. In the illustrated embodiment, blocking portion 425 comprises a series of generally longitudinal, meandering struts 426,427,428 independently connecting to tubular section 435 at one end and interconnected at the opposite end via a transverse strut 429.

The porous structure created by struts 426,427,428,429 is covered with a material suitable to: (i) withstand expansion of prosthesis 400, and (ii) block the opening 35 of aneurysm 30 after deployment. The nature of the material used for this purpose is not particularly restricted. Preferably, the material comprises Cardiothane 51™ (Kontron Instruments, Inc., Everett, Mass.), a medical grade polyurethane/silcone polymer which is known to be useful in intravascular devices (e.g., as a balloon material for intraaortic cardiac assist devices). Thus, a "bare" blocking portion 425 may be initially coated with a 5.7% weight:volume (w:v) solution of Cardiothane 51™ dissolved in an organic solvent (e.g., 2:1 tetrahydrofuran:1,4-dioxane). The initially coated blocking portion 425 may then be further covered with an 11.7% w:v solution of Cardiothane 51™ dissolved in the same solvent. When the polymer is dry, the struts of blocking portion are substantially embedded within the polyurethane-silicone cover. The covered blocking portion 425 may then be sterilized with ethylene-oxide. For more information about this approach, see "In Vivo Evaluation of Porous Versus Skinned Polyurethane-Polydimethylsiloxane Small Diameter Vascular Grafts" by Okoshi et al., *ASAIO Transactions* 1991; 37: M480–M481, the contents of which are hereby incorporated by reference.

Figure 24:
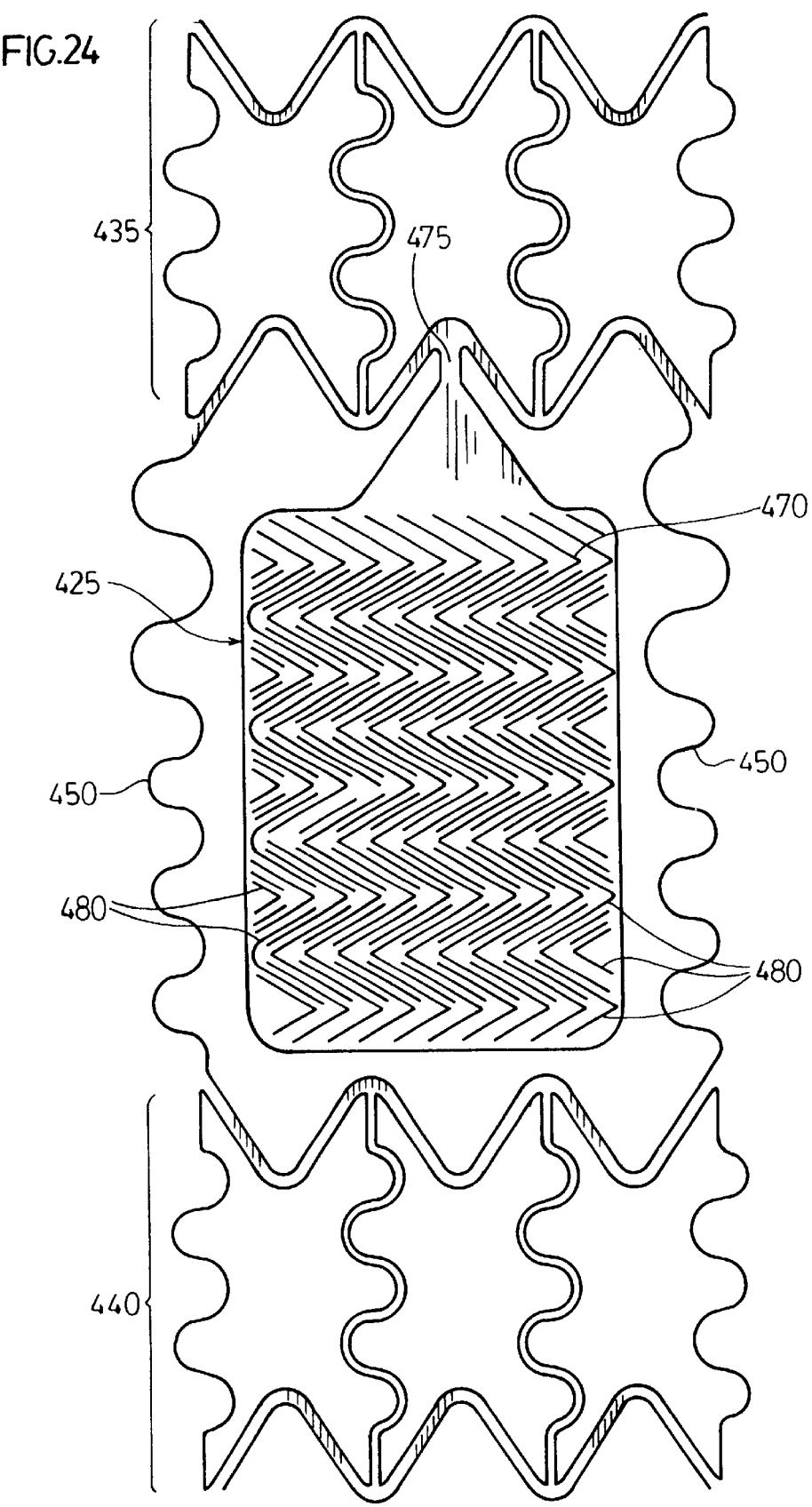
FIG. 24 illustrates an enlarged two-dimensional representation of another embodiment encompassed by the endovascular prosthesis illustrated in FIGS. 20–22.

FIG. 24 illustrates a two-dimensional representation of one embodiment of expandible prosthesis 400. In the illustrated embodiment, blocking portion 425 comprises a tab 470 connected to tubular section 435 at a connection point 475. As illustrated, a portion of tab 470 contains a series of tightly spaced microcuts 480. The selection of dimension, number and disposition of microcuts 480 is within the purview of a person skilled in the art and is chosen to optimize flexibility of tab 470 while limiting porosity therethrough of bodily fluids.

Other variations and modifications of the specific embodiments described hereinabove which do not depart from the scope and spirit of the invention will be immediately apparent to those of skill in the art having this specification in hand. For example, while in various of the illustrated embodiments, the leaf portion is shown pointing toward the proximal end of the prosthesis during delivery, this is not essential and, in some cases, a reverse orientation may be preferred. Further, while in various of the illustrated embodiments, the leaf portion comprises a head and a neck, the presence of the neck is not essential in all cases. Still further, while in various of the illustrated embodiments, a pair of expandable, annular rings is shown, it is possible to construct the prothesis using a single expandable anchoring means (e.g., annular ring, etc.) or 3 or more expandable anchoring means (e.g., annular rings, etc.). Still further, while in various of the illustrated embodiments, the leaf portion is substantially elongate and disposed parallel to the longitudinal axis of the prosthesis, it is possible to dispose the leaf portion such that it is orthogonal to the longitudinal axis of the prosthesis. Still further, while in various of the illustrated embodiments, the expansible portion of the body comprises a pair of rings having a porous structure, it is possible to use rings having a non-porous structure by folding down the rings and maintaining them in this state using a removable mechanical restraint which, when removed, allows the rings to unfold into a deployed state (in this embodiments, the rings would be dimensioned to their final implanted diameter and then folded down—see for example, WO-A-95/26695, the contents of which are hereby incorporated by reference). Other modifications which do not deviated from the spirit and scope of the invention will be immediately apparent to those of skill in the art having the present specification in hand.

What is claimed is:

1. A prosthesis for endovascular blocking of an aneurysmal opening, the prosthesis comprising:
   a body having a promixal end, a distal end and at least one expandable portion disposed therebetween the at least one expandable portion being expandable from a first, unexpanded state to a second, expanded state with a radially outward force thereon to urge the first expandable portion against a vascular lumen, and
   a leaf portion attached to the body,
   the leaf portion being independently moveable with respect to the body.

2. The prosthesis defined in claim 1, wherein the leaf portion comprises a substantially non-porous section.

3. The prosthesis defined in claim 1, wherein the at least one tubular expandable portion is porous.

4. The prosthesis defined in claim 1, wherein the body comprises at least a pair of opposed tubular expandable portions.

5. The prosthesis defined in claim 4, wherein the opposed tubular expandable portions are connected to one another by connection means.

6. The prosthesis defined in claim 4, wherein the opposed tubular expandable portions are connected to one another by at least one wire.

7. The prosthesis defined in claim 4, wherein the leaf portion is connected to one of the opposed tubular expandable portions.

8. The prosthesis defined in claim 4, wherein the opposed tubular expandable portions comprise a porous surface.

9. The prosthesis defined in claim 4, wherein the opposed tubular expandable portions, the connection means and the leaf portion are integrally formed.

10. The prosthesis defined in claim 1, wherein the body is a tube.

11. The prosthesis defined in claim 1, wherein the body is a porous tube.

12. The prosthesis defined in claim 1, wherein the tube is constructed from a plastically deformable material.

13. The prosthesis defined in claim 12, wherein the tube is constructed from a selfexpanding material.

14. The prosthesis defined in claim 11, wherein the leaf portion is a cut-out of the tube to define an opening in the body in the second position.

15. The prosthesis defined in claim 1, wherein the leaf portion comprises a head.

16. The prosthesis defined in claim 1, wherein the leaf portion comprises a neck which interconnects the head and the body.

17. The prosthesis defined in claim 1, wherein the head is wider than the neck.

18. The prosthesis defined in claim 1, wherein the leaf portion further comprises a pharmaceutically acceptable adhesive on a surface thereof.

19. The prosthesis defined in claim 1, wherein the leaf portion further comprises mechanical adjustment means to adjust the position of the leaf portion with respect to the body.

20. The prosthesis defined in claim 19, wherein the adjustment means comprises a wire attached to the leaf portion.

21. The prosthesis defined in claim 20, wherein the wire is attached to the leaf portion at a point distal to the point at which the leaf portion is connected to the body.

22. The prosthesis defined in claim 1, wherein the leaf portion further comprises a pharmaceutically acceptable compound capable of expanding and entering an opening in the aneurysm.

23. The prosthesis defined in claim 1, wherein the pharmaceutically acceptable compound expands upon activation.

24. The prosthesis defined in claim 1, wherein the pharmaceutically acceptable compound expands upon electrical activation.

25. The prosthesis defined in claim 1, wherein the leaf portion comprises an aperture for receiving guide means for navigating the prosthesis to a target location.

26. A method for endovascular blocking of an aneurysmal opening with a prosthesis comprising: a body having a promixal end, a distal end and at least one expandable portion disposed therebetween, and a leaf portion attached to the body, the method comprising the steps of:
   disposing the prosthesis on a catheter;
   inserting the prosthesis and catheter within a body passageway by catheterization of the body passageway;
   translating the prosthesis and catheter to a target body passageway at which the aneurysm opening is located;
   exerting a radially outward expansive force on the at least one expandable portion such that the at least one expandable portion is urged against the target body passageway;
   urging the leaf portion against the aneurysmal opening thereby blocking the aneurysmal opening.

27. A prosthesis for endovascular blocking of an aneurysmal opening, the prosthesis comprising:
   a body having a longitudinal axis comprising at least one expandable portion, the at least one expandable portion being expandable from a first, unexpanded state to a second, expanded state with a radially outward force thereon to urge the first expandable portion against a vascular lumen, and
   a leaf portion attached to the body,
   the body being flexible between: (i) a first position in which the at least one expandable portion and the leaf portion are aligned along the longitudinal axis, and (ii) a second position in which the at least one expandable portion and the leaf are unaligned along the longitudinal axis.

* * * * *